United States Patent [19]

Azuma et al.

[11] Patent Number: 4,902,334

[45] Date of Patent: Feb. 20, 1990

[54] REGULATION OF PLANT METABOLISM BY ALPHA, BETA-OR BETA, GAMMA-UNSATURATED CARBOXYLIC ACIDS OR DERIVATIVES THEREOF

[75] Inventors: Shizuo Azuma, Iwakuni; Toshiyuki Hiramatsu, Iwakuni; Teizo Yamaji, Iwakuni; Yataro Ichikawa, Tokorozawa, all of Japan

[73] Assignee: Teijin Limited, Osaka, Japan

[21] Appl. No.: 666,633

[22] Filed: Oct. 31, 1984

[30] Foreign Application Priority Data

| Dec. 21, 1983 | [JP] | Japan | 58-239698 |
| Feb. 10, 1984 | [JP] | Japan | 59-21560 |
| Sep. 10, 1984 | [JP] | Japan | 59-188106 |
| Sep. 10, 1984 | [JP] | Japan | 59-188107 |
| Sep. 10, 1984 | [JP] | Japan | 59-188108 |

[51] Int. Cl.$^4$ .............. C07C 101/02; C07C 69/73; C07C 149/20; C07C 67/02

[52] U.S. Cl. .............. 71/88; 560/172; 560/183; 560/152; 560/262; 560/62; 560/60; 562/574; 562/579; 562/598; 562/155; 562/183; 562/156; 546/226; 546/187; 546/190; 546/193; 546/235; 546/233; 546/300; 546/207; 546/208; 546/256; 546/261; 546/281; 546/268; 546/291; 546/301; 546/288; 71/103; 71/90; 71/92; 71/94; 71/95; 71/105; 71/106; 71/113; 71/98; 71/100; 71/118; 71/76; 558/440; 558/443; 558/441; 558/445; 558/253; 558/254; 548/573; 548/524; 548/517; 548/540; 548/568; 548/569; 549/419; 549/420; 549/553; 549/561; 549/551

[58] Field of Search .............. 548/524, 517, 540, 568, 548/569; 549/551, 419, 420, 553, 561; 546/187, 190, 193, 235, 233, 300, 207, 208, 256, 261, 281, 268, 291, 301, 226; 560/172, 183, 152, 262; 562/574, 579, 598; 260/239 BF, 239 B, 400 T; 71/76, 103, 88, 90, 92, 94, 95, 105, 106, 113, 98, 100, 118; 558/253, 254

[56] References Cited

U.S. PATENT DOCUMENTS

| 2,386,277 | 3/1975 | Berger et al. | 560/172 |
| 2,825,640 | 3/1958 | Northcraft | 71/70 |
| 2,859,239 | 11/1958 | Trapp et al. | 560/172 |
| 2,985,684 | 5/1961 | Pennino | 560/130 |
| 3,176,038 | 3/1965 | Zachry et al. | 560/183 |
| 3,231,598 | 1/1966 | Berezin | 560/172 |
| 3,668,242 | 6/1972 | Weil et al. | 560/172 |
| 3,772,384 | 11/1973 | Knowles | 560/172 |
| 3,801,612 | 4/1974 | Willy et al. | 568/678 |
| 3,922,287 | 11/1975 | Pawson et al. | 560/135 |
| 3,991,112 | 11/1976 | Donnell | 560/172 |
| 4,052,423 | 10/1977 | Larock | 560/172 |

FOREIGN PATENT DOCUMENTS

| 0007089 | 1/1980 | European Pat. Off. | 560/172 |
| 45-31320 | 10/1970 | Japan | 560/172 |
| 6703020 | 9/1967 | Netherlands | 560/172 |
| 6703449 | 9/1967 | Netherlands | 560/172 |
| 6811769 | 2/1969 | Netherlands | 560/172 |
| 7009285 | 1/1971 | Netherlands | 560/172 |
| 218563 | 8/1968 | U.S.S.R. | 560/172 |
| 1243987 | 8/1971 | United Kingdom | 71/70 |
| 2101600 | 1/1983 | United Kingdom | 560/172 |

OTHER PUBLICATIONS

Nagano, Agric. Biol. Chem. 44(9) 2095-2098 (1980).
Weir et al., J. Org. Chem., vol. 45, 1980, pp. 4926-4931.
Krasnaya et al., Chem. Abs., vol. 79, 1973, 79:179981.
Hasegawa, Chem. Abs., vol. 95, 1981, 95:80199W.
Kishida, Chem. Abs., vol. 72, 1970, 72:78722t.
Strave, et al., J. Org. Chem., vol. 47, 1982, pp. 2109-2113.
Nozaki et al., CA 91:39,070b (1979).
Bunnell et al., CA 87:133832r (1977).

Primary Examiner—Mary C. Lee
Assistant Examiner—Robert C. Whittenbaugh
Attorney, Agent, or Firm—Wenderoth, Lind & Ponack

[57] ABSTRACT

A plant metabolism regulating agent comprising as an active ingredient an alpha,beta or beta,gamma-unsaturated carboxylic acid or its derivative. It is useful for controlling the metabolism of a plant, facilitating the growth of a beneficial plant such as cereals by inhibiting the growth of undesirable plants or eradicating them, regulating the growth of a plant and dwarfing a plant.

25 Claims, No Drawings

REGULATION OF PLANT METABOLISM BY ALPHA, BETA-OR BETA, GAMMA-UNSATURATED CARBOXYLIC ACIDS OR DERIVATIVES THEREOF

This invention relates to a plant metabolism regulating agent comprising an alpha,beta- or beta,gamma-unsaturated carboxylic acid or its derivaive as an active ingredient.

The prior art literature discloses that alpha,beta- or beta,gamma-unsaturated carboxylic acids or their derivatives can be an active ingredient of a herbicide.

Let us assume that alpha,beta-unsaturated carboxylic acids or their derivatives are expressed by the following formula.

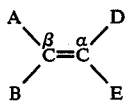

By using the above formula, alpha,beta-unsaturated carboxylic acids or their derivatives which have been known as active ingredients of herbicides are described below.

Japanese Patent Publication No. 31320/1970 discloses alpha,beta-unsaturated carboxylic acids of the formula in which A bonded to the carbon atom at the beta-position is a linear or branched alkyl group having 3 to 10 carbon atoms, B is a hydrogen atom or an alkyl group having 1 to 3 carbon atoms, D is a hydrogen atom, and E is a carboxyl group, their lower alkyl esters, amides and metal or ammonium salts as non-selective contact-type herbicides.

U.S. Pat. No. 2,859,239 discloses that compounds of the formula in which A bonded to the carbon atom at the beta-position is a 3-cyclohexen-1-yl group, B and D are hydrogen atoms and E is a carboxyl, cyano, carbalkoxy or carbalkenoxy group having utility as herbicides for the control of undesirable vegetation.

U.S. Pat. No. 4,052,423 discloses a process for producing alpha,beta-unsaturated carboxylic acid esters by reacting the corresponding vinylmercuric halides, carbon monoxide and corresponding alcohols in the presence of a noble metal carbonylation promoter. The specification states that U.S. Pat. No. 2,859,239 cited above discloses that cinnamic acid esters are useful perfume aromatics, insecticides, herbicides, parasiticides, bactericides and fungicides.

British Pat. No. 2,101,600 discloses compounds of the following formula

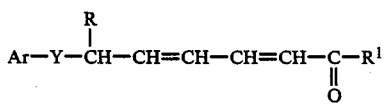

wherein R is hydrogen or methyl, Y is an oxygen or divalent sulfur atom, $R^1$ or $OR^2$, $SR^2$ or $N(R^2)_2$ group, $R^2$ is hydrogen, $C_1$-$C_4$ alkyl, $C_3$-$C_6$ cycloalkyl, $C_2$-$C_4$ alkenyl, $C_2$-$C_4$ alkinyl, phenyl or benzyl, Ar is phenyl, pyridyl, naphthyl, quinoyl, phenoxyphenyl or pyridyloxyphenyl, and these groups may optionally be substituted by one or more substituents selected from hydrogen, $C_1$-$C_4$ alkyl, $C_1$-$C_4$ alkoxy, nitro, cyano, trifluoromethyl, acetoxy, acetamide and methoxycarbonyl, as herbicides or plant growth regulators.

British Pat. No. 2,101,600 discloses compounds of the formula given earlier in which A is an alkenyl group having 3 or 4 carbon atoms substituted by a specific aromatic oxy or thio group, B and D are hydrogen atoms and E is a carboxylic ester, thioester or amide.

U.S. Pat. No. 3,991,112 discloses that compounds of the formula in which A is a propenyl group substituted by a carboxylic hydrazide group, B is a hydrogen atom, D is a methyl group and E is a carboxylic hydrazide group are selectively effective against certain broad-leaved plants such as defoliants and herbicides.

U.S. Pat. No. 3,668,242 discloses compounds of the formula in which A is an optionally substituted phenoxy or naphthoxy group, B is a 1,2,2-trihaloethenyl group, D is halo, and E is a carboxyl group or a carboxylic salt, ester or amide group.

Dutch Pat. No. 6703020 discloses herbicidal and plant growth regulating compounds of the formula in which A is an ethenyl group substituted by a carbocyclic group, B is hydrogen or a $C_{1-4}$ lower alkyl group, D is a hydrogen atom and E is a carboxyl group or a carboxylic salt, ester or amide group.

Dutch Pat. No. 7009285 discloses plant growth regulators useful as herbicides and represented by the formula in which A is a beta-(1,2-epoxy-6,6-dimethyl-3-cyclohexen-1-yl)ethenyl group, B is a methyl group, D is a hydrogen atom and E is a carboxyl group or a carboxylic ester or amide group.

Dutch Pat. No. 6703449 discloses that 3-methyl-5-(1-hydroxy-4-oxo-2,6,6-trimethyl-2-cyclohexen-1-yl)-2,4-pentadienoic acid modifies or regulates the growth of plants.

Dutch Pat. No. 6811769 discloses that a plant growth regulating composition containing as an active ingredient a compound of the formula in which A is a beta-(1,2-epoxy-2,6,6-trimethylcyclohexanyl)ethenyl group, B and D are hydrogen or (halo)alkyl, and E is a carboxyl group or a carboxylic ester or amide group.

Agricultural Biological Chemistry 44 (9), 2695–2698 (1980) discloses 3-methyl-5-(1-hydroxy-5-propenyl-2-methyl)cyclohexen-1-yl)-2,4-pentadienic acid.

On the other hand, let us assume that beta, gamma-unsaturated carboxylic acids or their derivatives are expressed by the following formula.

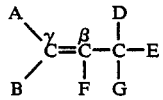

By using this formula, beta,gamma-unsaturated carboxylic acids or their derivatives which have been known as active ingredients of herbicides are described below.

European Pat. No. 7089 discloses a herbicide and/or a fungicides of the formula in which A, B and F are hydrogen atoms, D and G are a hydrogen atom or a methyl or ethyl group, and E is an anilide group.

U.S. Pat. No. 3,772,384 discloses a method of producing organic esters, and Example 1 of this patent describes the preparation of a mixture of methyl 3-butenate and methyl 2-butenate. The specification states that certain esters produced by this method are useful as polymer intermediates or herbicides. Methyl 3-butenate corresponds to a compound of the above formula in which A, B, D, F and G are hydrogen atoms and E is a methoxycarbonyl group.

U.S.S.R. Pat. No. 218,563 discloses that trichlorovinyl acetic acid corresponding to the formula in which A, B and F are chloro, D and G are hydrogen and E is a carboxyl group can be used as a herbicide.

U.S. Pat. No. 3,231,598 discloses that thio-carboxylic acid esters of the formula in which A, B, D and G are hydrogen atoms, F is methyl and E is n-propylthio are useful as chemical intermediates and herbicides.

U.S. Pat. No. 3,869,277 discloses that L-trans-2-amino-4-(2-aminoethoxy)-3-butenoic acid controls undesirable plants after emergence.

It is an object of this invention therefore to provide a plant metabolism regulating agent comprising a specific alpha,beta- or beta,gamma-unsaturated carboxylic acid or its derivative as an active ingredient.

Another object of this invention is to provide a plant metabolism regulating agent comprising as an active ingredient a compound basically characterized by a chemical structure in which a group bonded to the carbon atom at the beta-position in the case of an alpha,beta-unsaturated carboxylic acid or its derivative and a group bonded to the carbon atom at the gamma-position in the case of a beta,gamma-unsaturated carboxylic acid or its derivative are an aliphatic hydrocarbon group which may optionally be substituted and has at least one carbon-carbon unsaturated bond, and another group bonded to the carbon atom at the beta-position (in the case of the alpha,beta-compound) or the carbon atom at the alpha-position (in the case of the beta,gamma-compound) is a specific group such as an ester and an amide group.

Still another object of this invention is to provide a plant metabolism regulating agent having excellent selectivity which inhibits the growth of undesirable plants, whether monocotyledonous or dicotyledonous, or eradicate them without exerting substantially adverse effects on beneficial plants such as rice and corn.

Yet another object of this invention is to provide a plant metabolism regulating agent which can inhibit the growth of undesirable plants or eradicate them at low rates of application per unit area, for example at not more than 100 g/10 ares.

A further object of this invention is to provide a plant metabolism regulating which acts on buds after germination and at least inhibits the growth of undesirable plants, and therefore can create a condition in which beneficial plants can easily grow beyond the growth of the undesirable plants in areas where the undesirable and beneficial plants exist together.

A still further object of this invention is to provide a plant metabolism regulating agent which has low toxicity to animals and fish.

An additional object of this invention is to provide a plant metabolism regulating agent which can be easily produced at low costs.

Other objects and advantages of this invention will become apparent from the following description.

These objects and advantages of this invention are achieved in accordance with this invention by a plant metabolism regulating agent comprising as an active ingredient an alpha,beta- or beta,gamma-unsaturated carboxylic acid or its derivative represented by the general formula (I) below

wherein $R^1$ represents a hydrogen atom or a linear or branched aliphatic hydrocarbon group which may be substituted and has at least one unsaturated bond selected from carbon-carbon double and triple bonds and in which the main chain has 2 to 15 carbon atoms;

$R^2$ represents a group selected from the class consisting of a hydrogen atom, halogen atoms, a cyano group, a nitro group, hydrocarbon groups having 1 to 7 carbon atoms which may be substituted, groups $OR^7$, groups $SR^7$ and groups $NR^8R^9$, in which $R^7$ represents a hydrogen atom, a hydrocarbon group having 1 to 15 carbon atoms which may be substituted, a hydrocarbon-carbonyl group having 2 to 16 carbon atoms which may be substituted, a hydrocarbon-sulfonyl group having 1 to 15 carbon atoms which may be substituted or the group $HSO_2-$, and $R^8$ and $R^9$ are identical or different and each represents a hydrogen atom, a hydrocarbon group having 1 to 10 carbon atoms which may be substituted, a hydrocarbon-carbonyl group having 2 to 10 carbon atoms which may be substituted, or a hydrocarbon-sulfonyl group having 1 to 10 carbon atoms which may be substituted, or $R^8$ and $R^9$ together may form a ring together with the nitrogen atom to which they are bonded;

$R^3$ represents a group selected from said groups represented by $R^2$;

$R^4$ and $R^5$ are identical or different and each represents a group selected from said groups represented by $R^2$;

$R^6$ represents a group selected from the class consisting of groups $OR^{10}$, groups $SR^{10}$ and groups $NR^8R^9$, in which $R^{10}$ represents a hydrogen atom, one equivalent of a cation, or a hydrocarbon group having 1 to 15 carbon atoms which may be interrupted by an oxygen atom and may be substituted, and $R^8$ and $R^9$ are as defined; and n is 0 or 1 provided that (1) in the case of n=0, $R^1$ cannot be a hydrogen atom, and when $R^1$ has as the unsaturated bond a double bond conjugated with the double bond between the carbon atoms to which $R^1$ and $R^3$ are bonded, the number of carbon atoms of the main chain of $R^1$ cannot be not more than 4, and (2) in the case of n=1, when $R^1$, $R^2$ and $R^4$ are hydrogen atoms at the same time, $R^5$ cannot be a hydrogen atom or an unsubstituted hydrocarbon group having 1 to 15 carbon atoms, and when $R^4$ is a hydrogen atom and $R^5$ is the group $NR^8R^9$ in which $R^8$ and $R^9$ are hydrogen atoms, $R^2$ cannot be a hydrocarbonoxy group ($OR^7$) having 1 to 15 carbon atoms having as a substituent the group $NR^8R^9$ in which $R^8$ and $R^9$ are hydrogen atoms.

The alpha,beta- or beta,gamma-unsaturated carboxylic acid or its derivative used as the active ingredient in this invention is represented by the above general formula (I).

In Formula (I), $R^1$ is a hydrocarbon atom, or a linear or branched aliphatic hydrocarbon group which may be substituted and in which the main chain has 2 to 15, preferably 2 to 13, carbon atoms. The aliphatic hydrocarbon group should have at least one of carbon-carbon double and triple bonds. The main chain of the aliphatic hydrocarbon denotes that straight chain portion which has the largest number of carbon atoms.

The aliphatic hydrocarbon group may preferably have 1 to 5 double and triple bonds. These unsaturated bonds may exist on the main chain or side chains, but preferably the main chain of the aliphatic hydrocarbon group has at least one unsaturated bond.

The aliphatic hydrocarbon group may be substituted by a substituent which is preferably a halogen atom, a cyano group, a nitro group, an epoxy group, a cycloalkyl or cycloalkenyl group having 5 to 7 carbon atoms as ring members, a phenyl group, a naphthyl group, the group $-OR^{11}$ or the group $-SR^{11}$ (wherein $R^{11}$ represents a hydrogen atom, a hydrocarbon group having 1 to 15 carbon atoms which may be substituted, or a hydrocarbon-carbonyl group having 2 to 16 carbon atoms which may be substituted) or the group $NR^8R^9$ (Wherein $R^8$ and $R^9$ are identical or different, and each represents a hydrogen atom, a hydrocarbon group having 1 to 10 carbon atoms which may be substituted, a hydrocarbon-carbonyl group having 2 to 10 carbon atoms which may be substituted or a hydrocarbon-sulfonyl group having 1 to 10 carbon atoms which may be substituted, or $R^8$ or $R^9$ together may form a ring together with the nitrogen atom to which they are bonded).

The halogen atom denotes fluorine, chlorine, bromine, iodine, etc. Examples of the cycloalkyl or cycloalkenyl group having 5 to 7 carbon atoms as ring members are cyclopentyl, cyclohexyl, cycloheptyl, cyclopentenyl, cyclohexenyl, cyclohexadienyl and cycloheptenyl. The $C_1$–$C_{15}$ hydrocarbon group represented by $R^{11}$ in the groups $-OR^{11}$ and $-SR^{11}$ is, for example, an alkyl group having 1 to 15 carbon atoms, an alkenyl or alkynyl group having 2 to 15 carbon atoms, a cycloalkyl or cycloalkenyl group having 3 to 7 carbon atoms, a phenyl group or a naphthyl group. The $C_1$–$C_{15}$ alkyl group may be linear or branched, and includes, for example, methyl, ethyl, propyl, butyl, hexyl, octyl, decyl, dodecyl, tetradecyl and pentadecyl. The $C_2$–$C_{15}$ alkenyl or alkynyl group may be a linear or branched, and have a double or triple bond at an arbitrary position. Examples of such groups are ethenyl, ethynyl, propenyl, propynyl, octenyl, decenyl and decynyl. Examples of the $C_3$–$C_7$ cycloalkyl or cycloalkenyl group are cyclopropyl, cyclopentyl, cyclohexyl, cycloheptyl, cyclopentenyl, cyclohexenyl and cycloheptenyl.

The above groups represented by $R^{11}$ may in turn be substituted by various substituents. Examples include cycloalkyl or cycloalkenyl groups having 5 to 7 carbon atoms as ring members, a phenyl group, a phenoxy group, a pyridyloxy group and a naphthyl group when $R^{11}$ represents a $C_1$–$C_{15}$ alkyl group, or a $C_2$–$C_{15}$ alkenyl or alkynyl group; alkyl groups having 1 to 7 carbon atoms, alkenyl groups having 2 to 7 carbon atoms, a phenyl group, a naphthyl group, a phenoxy group or a pyridyloxy group when $R^{11}$ is a cycloalkyl or cycloalkenyl group having 3 to 7 carbon atoms; and alkyl groups having 1 to 7 carbon atoms, alkenyl groups having 2 to 7 carbon atoms, cycloalkyl or cycloalkenyl groups having 5 to 7 carbon atoms as ring members, a phenoxy group and a pyridyloxy group when $R^{11}$ is a phenyl group. The aforesaid phenoxy group and pyridyloxy groups may be substituted by a halogen atom, a cyano group, a nitro group, an unsubstituted or halogen-substituted alkyl group having 1 to 4 carbon atoms, the group $OR^{11}$, the group $SR^{11}$ or the group $NR^8R^9$.

Examples of the $C_2$–$C_{16}$ hydrocarbon-carbonyl group represented by $R^{11}$ of the groups $-OR^{11}$ and $-SR^{11}$ include alkylcarbonyl groups having 2 16 carbon atoms, alkynyl-carbonyl groups having 3 to 16 carbon atoms, cycloalkyl-carbonyl or cycloalkenylcarbonyl groups having 4 to 8 carbon atoms and a benzoyl group. These groups may in turn be substituted. Specific examples of these groups and substituents therefor will be apparent from the examples given above with regard to the $C_1$–$C_{15}$ hydrocarbon groups.

As stated above the groups $R^8$ and $R^9$ of the group $-NR^8R^9$ are identical or different and each represents a hydrogen atom, a $C_1$–$C_{10}$ hydrocarbon group which may be substituted, a $C_2$–$C_{10}$ hydrocarbon-carbonyl group which may be substituted or a $C_1$–$C_{10}$ hydrocarbon-sulfonyl group which may be substituted. Or when taken together, $R^8$ and $R^9$ may form a ring together with the nitrogen atom to which they are bonded.

The $C_1$–$C_{10}$ hydrocarbon group may, for example, be an alkyl group having 1 to 10 carbon atoms, an alkenyl or alkynyl group having 2 to 10 carbon atoms, a cycloalkyl or cycloalkenyl group having 3 to 7 carbon atoms, or a phenyl group.

Examples of the $C_2$–$C_{10}$ hydrocarbon-carbonyl group include alkylcarbonyl groups having 2 to 10 carbon atoms, alkylcarbonyl groups having 3 to 10 carbons, cycloalkylcarbonyl groups having 4 to 8 carbon atoms, cycloalkenylcarbonyl groups having 4 to 8 carbon atoms and a benzyl group.

Specific examples of the $C_1$–$C_{10}$ hydrocarbon groups and $C_2$–$C_{10}$ hydrocarbon-carbonyl groups will be apparent from the specific examples given above to $R^{11}$.

Examples of the $C_1$–$C_{10}$ hydrocarbon-sulfonyl group include alkylsulfonyl groups having 1 to 10 carbon atoms, alkenylsulfonyl groups having 2 to 10 carbon atoms, cycloalkylsulfonyl groups having 3 to 7 carbon atoms, cycloalkenylsulfonyl groups having 3 to 7 carbon atoms, and a phenylsulfonyl group. The $C_1$–$C_{10}$ alkylsulfonyl groups may be linear or branched, and include, for example, methylsulfonyl, ethylsulfonyl, propylsulfonyl, butylsulfonyl, octylsulfonyl and decylsulfonyl. The $C_2$–$C_{10}$ alkenylsulfonyl groups may be linear and branched, and include, for example, vinylsulfonyl, propenylsulfonyl, butenylsulfonyl and decenylsulfonyl. Examples of the $C_3$–$C_7$ cycloalkylsulfonyl or cycloalkenylsulfonyl groups are cyclopropylsulfonyl, cyclopentylsulfonyl, cyclohexylsulfonyl, cyclohexenylsulfonyl and cycloheptylsulfonyl.

The above groups represented by $R^8$ and $R^9$ may be substituted. Substituents for them may be the same substituents as described above with regard to the groups $R^{11}$.

When $R^8$ and $R^9$ form a ring together with the nitrogen atom to which they are bonded, the ring may further contain a heteroatom such as $-O-$, $-S-$, or $-NY-$ (in which Y is a hydrogen atom or a lower alkyl group having 1 to 4 carbon atoms) in addition to the aforesaid nitrogen atom. The ring may preferably have 5 to 7 carbon atoms.

In formula (I), $R^2$ represents a hydrogen atom, a halogen atom, a cyano group, a nitro group, a hydrocarbon group having 1 to 7 carbon atoms which may be substituted, the group $-OR^7$, the group $-SR^7$ (in which $R^7$ is a hydrogen atom, a hydrocarbon group having 1 to 15 carbon atoms which may be substituted, a hydrocarbon-carbonyl group having 2 to 16 carbon atoms which may be substituted, a hydrocarbonsulfonyl group having 1 to 15 carbon atoms which may be substituted or the group HSO$_2$—) or the group —NR$^8$R$^9$ (in which R$^8$ and R$^9$ are as defined above).

Examples of the group R$^7$ include alkyl groups having 1 to 15 carbon stoms, alkenyl groups having 2 to 15 carbon atoms, cycloalkyl groups having 5 to 7 carbon atoms as ring members, cycloalkenyl groups having 5 to 7 carbon atoms as ring members, a phenyl group, a naphthyl group, aliphatic hydrocarbon-carbonyl group having 1 to 16 carbon atoms such as alkylcarbonyl or alkenylcarbonyl groups, a benzoyl group, a naphthylcarbonyl group, alkylsulfonyl groups having 1 to 15 carbon atoms, a phenylsulfonyl group and a naphthylsulfonyl group. These groups may be substituted. Specific examples of R$^7$ and substituents therefor will be apparent from the specific examples given above to R$^{11}$.

R$^3$ is selected from the groups R$^2$ described above. R$^4$ and R$^5$ are identical or different, and each is selected from the groups R$^2$ described above.

R$^6$ represents the group —OR$^{10}$, —SR$^{10}$ (in which R$^{10}$ represents a hydrogen atom, one equivalent of a cation, or a C$_1$-C$_{15}$ hydrocarbon group which may be interrupted by an oxygen atom and may be substituted), or the group —NR$^8$R$^9$ (in which R$^8$ and R$^9$ are as defined).

One equivalent of a cation represented by the group R$^{10}$ is, for example, an alkali metal cation such as Li$^+$, Na$^+$ or K$^+$, an alkaline earth metal cation such as ½Ca$^{++}$, ½Mg$^{++}$ or ½Ba$^{++}$, or a primary, secondary, tertiary or quaternary ammonium cation such as NR$_4^+$ (in which R's are identical or different and each represents a hydrogen atom, an alkyl group having 1 to 6 carbon atoms, a phenyl group or a benzyl group).

Examples of the C$_1$-C$_{15}$ hydrocarbon group include alkyl groups having 1 to 15 carbon atoms, alkyl groups having 4 to 15 carbon atoms and interrupted by an oxygen atom, alkenyl groups having 2 to 15 carbon atoms, alkynyl groups having 2 to 15 carbon atoms, cycloalkyl groups having 5 to 7 carbon atoms as ring members, cycloalkenyl groups having 5 to 7 carbon atoms as ring members, a phenyl group and a naphthyl group.

Preferred alkyl group having 4 to 15 carbon atoms and interrupted by an oxygen atom are those represented by the following formula

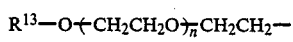

wherein R$^3$ represents a methyl or ethyl group, and n is a number that makes the total of the carbon atoms of the above group 4 to 15.

Specific examples of the other groups which are included within the C$_1$-C$_{15}$ hydrocarbon groups will be apparent from the specific examples given to R$^{11}$. These C$_1$-C$_{15}$ hydrocarbon groups may be substituted. Substituents therefor may be the same substituents as described above with regard to R$^{11}$.

In general formula (I), n is 0 or 1. When n is 0, the above general formula represents alpha,beta-unsaturated carboxylic acids of their derivatives. In this case, R$^1$ cannot be a hydrogen atom. Furthermore, when R$^1$ has a double bond conjugated with the double bond between carbon atoms to which R$^1$ and R$^3$ are bonded, the number of carbon atoms of the main chain of R$^1$ cannot be not more than 4. The compounds so excluded from general formula (I) tend to have poor selectivity for plants.

When n is 1 in general formula (I), the formula represents beta,gamma-unsaturared carboxylic acids of their derivatives. In this case, for the same reason as above, when R$^1$, R$^2$ and R$^4$ are hydrogen atoms at the same time, R$^5$ cannot be a hydrogen atom or an unsubstituted hydrocarbon group having 1 to 15 carbon atoms. Furthermore, when R$^4$ is a hydrogen atom, and R$^5$ is —NH$_2$, R$^2$ cannot be a C$_1$-C$_{15}$ hydrocarbonoxy group having —NH$_2$ as a substituent.

According to the above definition of n in formula (I), the present invention provides a plant metabolism regulating agent comprising as an active ingredient an alpha,beta-unsaturated carboxylic acid or its derivative represented by the following formula (I)-a

wherein R$^1$, R$^2$, R$^3$, and R$^6$ are as defined in formula (I), and a plant metabolism regulating agent comprising as an active ingredient beta,gamma-unsaturated carboxylic acid represented by the following formula (I)-b

wherein R$^1$, R$^2$, R$^3$, R$^4$, R$^5$ and R$^6$ are as defined above.

In formula (I)-a, R$^1$ is preferably a C$_2$-C$_{15}$ linear or branched aliphatic hydrocarbon group substituted by a hydrocarbon-carbonyloxy group having 2 to 16 carbon atoms. Of course, such an aliphatic hydrocarbon group has at least on unsaturated bond selected from carbon-carbon double and triple bonds.

In formula (I)-b, R$^5$ is a group represented by OR$^7$ or

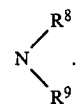

Preferably, R$^7$ is a hydrocarbon-carbonyl group which may be substituted, and R$^8$ and R$^9$ are preferably hydrocarbon-carbonyl groups having 2 to 10 carbon atoms.

Preferably, the C$_2$-C$_{16}$ hydrocarbon-carbonyloxy group, the C$_2$-C$_{16}$ hydrocarbon-carbonyl group and the C$_2$-C$_{10}$ hydrocarbon-carbonyl group are in turn substituted by substituted aromatic oxy groups. Preferred examples of the substituted aromatic oxy groups are phenoxy, naphthyloxy, phenoxyphenoxy and pyridyloxyphenoxy groups which are substituted by substituents selected from the class consisting of halogen atoms, a cyano group, a nitro group, unsubstituted or halogen-substituted alkyl groups having 1 to 4 carbon atoms, the groups —OR$^{11}$, the groups —SR$^{11}$ and the groups —R$^8$R$^9$.

Specific examples of the compounds of formula (I) are given below according to n=o (alpha,beta-unsaturated carboxylic acids of their derivatives) and n=1(beta,gamma-unsaturated carboxylic acids or their derivatives).

A. n=O (alpha,beta-unsaturated carboxylic acid or its derivative)

A-1. When $R^1$ contains one double bond and $R^2$ is H.
(100) Deca-2,9-dienoic acid
(102) Tetradeca-2,4dienoic acid
(104) Methyl 7-phenyl-octa-2,4,6-trienoate
(106) Methyl 7-(1-naphty)-octa-2,4,6-trienoate
(108) Methyl 7-cyclohexyl-octa-2,4,6-trienoate
(110) Methyl 7-(1-cyclohexyl)-octa-2,4,6-trienoate
(114) Methyl 5,9-dimethyl-8-nitro-deca-2,9-dienoate
(116) Methyl 8-cyano-5,9-dimethyl-deca-2,9-dienoate
(118) Methyl 8-bromo-5,9-dimethyl-deca-2,9-dienoate
(120) Methyl 10-bromo-5,9-dimethyl-deca-2,8-dienoate
(122) Methyl 10-amino-5,9-dimethyl-deca-2,8-dienoate
(124) Methyl 8-amino-5,9-dimethyl-deca-2,9-dienoate
(126) Methyl 8-mercapto-5,9-dimethyl-deca-2,9-dienoate
(130) 5,9-Dimethyl-8-(2,4-dichlorophenoxyacetyloxy)-deca-2,9-dienoic acid
(132) Sodium 5,9-dimethyl--8-(2,4-dichlorophenoxyacetyloxy)-deca-2,9-dienoate
(134) Iso-propylammonium 5,9-dimethyl-8-(2,4-dichlorophenoxyacetyloxy)-deca-2,9-dienoate
(136) Ethyl 8-(2,4-dichlorophenoxyacetyloxy)-octa-2,4-dienoate
(138) Ethyl 9,10-epoxy-8-(2,4-dichlorophenoxyacetyloxy)-5,9-dimethyl-deca-2,4-dienoate
(140) Methyl 5-methyl-4-(2,4-dichlorophenoxyacetyloxy)-hexa-2,5-dienoate
(142) Ammonium 5,9-dimethyl-8-(2,4-dichlorophenoxyacetyloxy)-deca-2,9-dienoate
(144) S-Ethyl 5,9-dimethyl-8-(2,4-dichlorophenoxyacetyloxy-deca-2,9-dienethioate
(146) Methyl 5,9-dimethyl-8-(2,4-dichlorophenoxyacetylthio)-deca-2,9-dienoate
(148) Methyl 8-(2,4-dichlorophenoxyacetylamino)-5,9-dimethyl)-deca-2,9-dienoate
(150) Methyl 10-(2,4-dichlorophenoxyacetylamino)-5,9-dimethyl-deca-2,8-dienoate
(152) Methyl 8-(2,4-dichlorophenoxyacetylamino)-5,9-dimethyl-deca-2,9-dienoate
(154) Methyl 2,5,9-trimethyl-8-(2,4-dichlorophenoxyacetyloxy)-deca-2,9-dienoate
(156) Methyl 2-amino-5,9-dimethyl-deca-2,8-dienoate
(158) Methyl 3-(2,4-dichlorophenoxyacetylamino)-5,9-dimethyl-deca-2,8-dienoate A-2. When $R^1$ contains one double bond and $R^2$ is other than H
(170) Methyl 6-hydroxy-3,7-dimethyl-octa-2,7-dienoate
(172) Methyl 6-amino-3,7-dimethyl-octa-2,7-dienoate
(174) Methyl 3,7-dimethyl-6-(2,4-dichlorophenoxyacetyloxy)-octa-2,7-dienoate
(176) Methyl 6-(2,4-dichlorophenoxyacetylamino)-3,7-dimethyl-octa-2,7-dienoate
(178) Methyl 5-methyl-3-penthyl-4-(2,4-dichlorophenoxyacetyloxy)-hexa-2,5-dienoate
(180) Methyl 5,9-dimethyl-8-(4-chloro-2-methylphenoxyacetyloxy)-deca-2,9-dienoate
(182) Methyl 3-cyano-5,9-dimethyl-deca-2,8-dienoate
(184) Methyl 3-mercapto-5,9-dimethyl-deca-2,8-dienoate
(186) Methyl 3-amino-5,9-dimethyl-deca-2,8-dienoate
(188) Ethyl 3-mesyloxy-trideca-2,12-dienoate
(190) Ethyl 3-2,4-dichlorophenoxyacetyloxy)-trideca-2,12-dienoate A-3. When $R^1$ contains at least 2 double bonds
(200) Ethyl 5,9-dimethyl-8-(2,4-dichlorophenoxyacetyloxy)-deca-2,4,9-trienoate
(202) Ethyl 5,9-dimethyl-8-(4-chloro-2-methylphenoxyacetyloxy)-deca-2,4,9-trienoate
(204) Ethyl 5,9-dimethyl-8-[2-(4-chloro-2-methylphenoxy)-propionyloxy]-deca-2,4,9-trienoate
(206) Methyl 5,9-dimethyl-8-(2,4-dichlorophenoxyacetyloxy)deca-2,4,9-trienoate
(208) Methyl 5,9-dimethyl-8-(4-chloro-2-methylphenoxyacetyloxy)-deca-2,4,9-trienoate
(210) 5,9-Dimethyl-8-(2,4-dichlorophenoxyacetyloxy)-deca-2,4,9-trienoic acid
(212) Sodium 5,9-dimethyl-8-(2,4-dichlorophenoxyacetyloxy)-deca-2,4,9-trienoate
(214) Iso-propyl ammonium 5,9-dimethyl-8-(2,4-dichlorophenoxyacetyloxy)-deca-2,4,9-trienoate
(216) Methyl 7,11,15-trimethyl-14-(2,4-dichlorophenoxyacetyloxy)-hexadeca-2,4,6,10,15-pentaenoate
(218) Methyl 5,9,13-trimethyl-12-(2,4-dichlorophenoxyacetyloxy)-tetradeca-2,4,8,13-tetraenoate
(220) Ethyl 5,9-dimethyl-2-nitro-8-(2,4-dichlorophenoxyacetyloxy)-deca-2,4,9-trienoate A-4. When $R^1$ contains a triple bond.
(230) Ethyl 6-hydroxy-hexa-2-ene-4-ynoate
(232) Ethyl 6-bromo-hexa-2-ene-4-ynoate
(234) Methyl 6-hydroxy-hexa-2-ene-4-ynoate
(236) Methyl 6-bromo-hexa-2-ene-4-ynoate
(238) Ethyl 6-chloro-hexa-2-ene-4-ynoate
(240) Methyl 6-chloro-hexa-2-ene-4-ynoate
(242) 6-Bromo-hexa-2-ene-4-ynoic acid
(244) Sodium 6-bromo-hexa-2-ene-4-ynoate
(246) Isopropyl ammonium 6-bromo-hexa-2-ene-ynoate
(248) n-Butyl ammonium 6-bromo-hexa-2-ene-4-ynoate
(250) n-Octyl ammonium 6-bromo-hexa-2-ene-4-ynoate
(252) N-isopropyl 6-bromo-hexa-2-ene-4-ynamide
(254) Ethyl 2-bromo-6-hydroxy-hexa-2-ene-4-ynoate
(256) Ethyl 2-chloro-6-hydroxy-hexa-2-ene-4-ynoate
(258) Ethyl 2,6-dibromo-hexa-2-ene-4-ynoate
(260) Ethyl 2-bromo-6-chloro-hexa-2-ene-4-ynoate
(262) Ethyl 6-bromo-2-chloro-hexa-2-ene-4-ynoate
(264) Ethyl 2,6-dichloro-hexa-2-ene-4-ynoate
(266) Methyl 2-bromo-6-hydroxy-hexa-2-ene-4-ynoate
(268) Methyl 2-chloro-6-hydroxy-hexa-2-ene-4-ynoate
(270) Methyl 2,6-dibromo-hexa-2-ene-4-ynoate
(272) Methyl 2-bromo-6-chloro-hexa-2-ene-4-ynoate
(274) Methyl 6-bromo-2-chloro-hexa-2-ene-4-ynoate
(276) Ethyl 2-cyano-6-(2-tetrahydropyranyloxy)hexa-2-ene-4-ynoate
(278) Ethyl 2-cyano-6-hydroxy-hexa-2-ene-4-ynoate
(280) Ethyl 6-bromo-2-cyano-hexa-2-ene-4-ynoate
(282) n-Octyl 6-(2-tetrahydropyranyloxy)-hexa-2-ene-4-ynoate
(284) n-Octyl 6-hydroxy-hexa-2-ene-4-ynoate
(286) n-Octyl 6-bromo-hexa-2-ene-4-ynoate
(288) Ethyl 6-acetoxy-hexa-2-ene-4-ynoate
(290) Ethyl 6-benzoyloxy-hexa-2-ene-4-ynoate
(292) Ethyl 6-mesyloxy-hexa-2-ene-4-ynoate
(294) Ethyl 6-(2,4-dichloro-phenoxy)-hexa-2-ene-4-ynoate
(296) Ethyl 6-[4-(2,4-dichlorophenoxy)phenoxy]-hexa-2-ene-4-ynoate
(298) Ethyl 6-(4-benzyloxyphenoxy)-hexa-2-ene-4-ynoate
(300) [2-(2-Ethoxyethyloxy)ethyl]-6-(2-tetrahydropyranyloxy)-hexa-2-ene-4-ynoate
(302) [2-(2-ethoxyethyloxy)ethyl]-6-hydroxy-hexa-2-ene-4-ynoate (304) [2-(2-Ethoxyethyloxy)ethyl]-6-bromo-hexa-2-ene-4-ynoate
(306) Ethyl 6-(2,4-dichlorophenoxyacetyloxy)-hexa-2-ene-4-ynoate
(308) [2-(2-ethoxyethyloxy)ethyl]-6-(2,4-dichlorophenoxyacetyloxy)hexa-2-ene-4-ynoate
(310) Ethyl 6-(4-chloro-2-methylphenoxyacetyloxy)-hexa-2-ene-4-ynoate
(312) Ethyl 6-(2,4,5-trichlorophenoxyacetyloxy)-hexa-2-ene-4-ynoate
(314) Ethyl 6-[2-(4-chloro-2-methylphenoxy)propionyloxy]-hexa-2-ene-4-ynoate
(316) Ethyl 6-(2-naphthoxyacetyloxy)-hexa-2-ene-4-ynoate
(318) Ethyl 6-[2-(4-(2,4-dichlorophenoxy)phenoxy)propionyloxy]-hexa-2-ene-4-ynoate
(320) [2-(2-ethoxyethyloxy)ethyl]-6-(4-chloro-2-methylphenoxyacetyloxy)-hexa-2-ene-4-ynoate
(322) [2-(2-ethoxyethyloxy)ethyl]-6-(2,4,5-trichlorophenoxyacetyloxy)-hexa-2-ene-4-ynoate
(324) [2-(2-ethoxyethyloxy)ethyl]-6-[2-(4-chloro-2-methylphenoxy)propionyloxy]-hexa-2-ene-4-ynoate
(326) [2-(2,4-Dichlorophenoxy)ethyl]-6-(2,4-dichlorophenoxyacetyloxy)-hexa-2-ene-4-ynoate
(328) N-(3,4-dichlorophenyl)-6-(2,4-dichlorophenoxyacetyloxy)-hexa-2-ene-4-ynamide
(330) Ethyl 8-(2,4-dichlorophenoxyacetyloxy)-octa-2-ene-4-ynoate
(332) n-Decyl 6-(2,4-dichlorophenoxyacetyloxy)-hexa-2-ene-4-ynoate
(334) N,N-diethyl 6-(2,4-dichlorophenoxyacetyloxy)-hexa-2-ene-4-ynamide
(336) 2-methyl-1-[6-(2,4-dichlorophenoxyacetyloxy)-hexa-2-ene-4-ynoyl]piperidine
(338) n-Octyl 6-(2,4-dichlorophenoxyacetyloxy)-hexa-2-ene-4-ynoate
(340) Ethyl 2-methyl-6-(2,4-dichlorophenoxyacetyloxy)-hexa-2-ene-4-ynoate A-5. When $R^1$ contains both a double bond and a triple bond
(350) Methyl 8-hydroxy-octa-2,4-diene-6-ynoate
(352) Methyl 8-(2,4-dichlorophenoxyacetyloxy)-octa-2,4-diene-6-ynoate B. n=1 (beta,gamma-unsaturated carboxylic acid and its derivative)

B-1. When both $R^1$ and $R^2$ are H
(360) 3-Methyl-2-nitro-3-butenoic acid
(362) 2-Amino-3-methyl-3-butenoic acid
(364) Methyl 3-methyl-2-nitro-3-butenoate
(366) Ethyl 3-methyl-2-(2,4-dichlorophenoxyacetyloxy)-3-butenoate
(368) Ethyl 3-methyl-2-(4-chloro-2-methylphenoxyacetyloxy)-3-butenoate
(370) 3-Methyl-2-(2,4-dichlorophenoxyacetyloxy)-3-butenoic acid
(372) Sodium 3-methyl-2-(2,4-dichlorophenoxyacetyloxy)-3-butenoate
(374) Iso-propyl ammonium 3-methyl-2-(2,4-dichlorophenoxyacetyloxy)-3-butenoate
(376) N-(3,4-dichlorophenyl)-3-methyl-2-(2,4-dichlorophenoxyacetyloxy)-3-butenamide
(377) Methyl 2-(2,4-dichlorophenoxyacetylamino)-3-methyl-3-butenoate
(378) n-Decyl 3-methyl-2-(2,4-dichlorophenoxyacetyloxy)-3-butenoate
(380) N,N-diethyl 3-methyl-2-(2,4-dichlorophenoxyacetyloxy)-3-butenamide
(382) Ethyl 3-methyl-2-(3-trifluoromethylphenoxyacetyloxy)-3-butenoate
(384) Ethyl 3-methyl-2-(2-naphthoxyacetyloxy)-3-butenoate
(386) Ethyl 3-methyl-2-[2-(4-(2,4-dichlorophenoxy)phenoxypropionyloxy]-3-butenoate
(388) Ethyl 3-methyl-2-(2-chloro-4-trifluoromethylphenoxyacetyloxy)-3-butenoate
(390) Ethyl 3-methyl-2-[2-(4-chloro-2-methylphenoxy)propionyloxy]-3-butenoate
(392) Ethyl 3-methyl-2-(2,4-dichlorophenoxyacetyloxy)-3-pentenoate
(394) Ethyl 3-methyl-2-(3-trifluoromethylphenoxyacetyloxy)-3-butenate
(396) Ethyl 3-methyl-2-[2-(2-naphtoxy)propionyloxy]-3-butenoate
(398) Ethyl 2-(2,4-dichlorophenoxyacetyloxy)-3-butenoate
(400) Ethyl 3-chloro-2-(2,4-dichlorophenoxyacetyloxy)-3-butenoate
(402) Ethyl 3-cyano-2-(2,4-dichlorophenoxyacetyloxy)-3-butenoate
(404) Ethyl 2,3-bis(2,4-dichlorophenoxyacetyloxy)-3-butenoate
(406) Ethyl 3-acetyloxy-2-(2,4-dichlorophenoxyacetyloxy)-3-butenoate B-2. When $R^1$ contains both a double bond and a triple bond
(410) Ethyl 3-methyl-2-(2,4-dichlorophenoxyacetyloxy)-hepta-3,6-dienoate
(412) Ethyl 3,7,11-trimethyl-2-(2,4-dichlorophenoxyacetyloxy)dodeca-3,6,10-trienoate
(414) Ethyl 3-methyl-2-(2,4-dichlorophenoxyacetyloxy)-hepta-3,6-dienoate
(416) Methyl 3,7,11-trimethyl-2-(2,4-dichlorophenoxyacetyloxy)dodeca-3,6,10-trienoate
(418) Ethyl 3-methyl-2-(2,4-dichlorophenoxyacetyloxy)-but-3-ene-5-ynoate
(420) Ethyl 4-chloro-3-methyl-2-(2,4-dichlorophenoxyacetyloxy)-3,5-heptadienoate
(422) Ethyl 3-methyl-4-nitro-2-(2,4-dichlorophenoxyacetyloxy)-3,5-heptadienoate
(424) Ethyl 4-acetylamino-3-methyl-2-(2,4-dichlorophenoxyacetyloxy)-3,5-heptadienoate
(426) Ethyl 3-methyl-4-(1-pyrrolidino)-2-(2,4-dichlorophenoxyacetyloxy)-3,5-heptadienate B-3. Others.
(430) Ethyl 3-methyl-2-(2,4-dichlorophenoxyacetyloxy)-3-heptanoate
(432) Ethyl 4-benzyloxy-3-methyl-2-(2,4-dichlorophenoxyacetyloxy)-3-butenoate
(434) Ethyl 4-acetyl-3-methyl-2-(2,4-dichlorophenoxyacetyloxy)-3-butenoate
(436) Ethyl 5-acetyloxy-3-methyl-2-(2,4-dichlorophenoxyacetyloxy)-3-pentenoate
(438) Ethyl 5-acetylamino-3-methyl-2-(2,4-dichlorophenoxyacetyloxy)-3-pentenoate The compounds of formula (I) include novel compounds as described below. The compounds of formula (I) can be produced by methods known per se.

A general process for producing the alpha,beta-unsaturated carboxylic acids or their derivatives of formula (I)-a is based, for example, on the Wittig reaction of carbonyl compounds of the following formula (II)

 (II)

wherein $R^1$ and $R^2$ are as defined above, with Wittig reagents of the following formula (III)

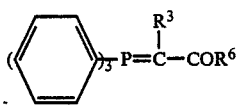 (III)

wherein $R^3$ and $R^6$ are as defined, (see Organic Reactions, Vol. 14, page 270).

Some of the carbonyl compounds of formula (II) are commercially available. Special carbonyl compounds of formula (II) can be produced, for example, by the following methods.

Compounds of formula (II) in which $R^1$ is a group having an unsaturated bond adjacent to the carbonyl group to which $R^1$ is bonded can be produced by subjecting a compound of the following formula

wherein $R^{14}$ is such a group that $R^{14}-C\equiv C$ satisfies the definition of $R^1$, and $\equiv$ represents a double or triple bond,
and a compound of the following formula

wherein $R^2$ is the same as defined above, to a Grignard reaction to form a compound represented by the following formula

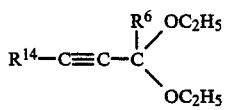

wherein $R^{14}$, $R^1$ and $\equiv$ are as defined above, and thereafter hydrolyzing the resulting compound under acidic conditions.

Compounds of formula (II) in which $R^1$ is a hydrocarbon group substituted by the group $OR^{11}$ can be produced, for example, by preparing a compound of the following formula

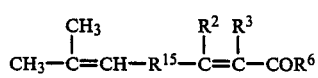

wherein $R^{15}$ is such a group that

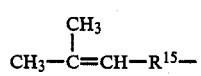

sastisfies the definition of $R^1$, and $R^2$, $R^3$ and $R^6$ are as defined above,
by the Wittig reaction, epoxidizing the compound with a peroxide such as m-chloroperbenzoic acid to form a compound of the following formula

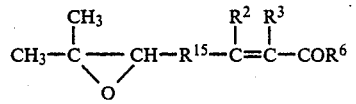

thermally decomposing the resulting compound, for example, by the method described in Agricultural Biological Chemistry, 44 (11), 2709 (1980) to form a compound of the following formula

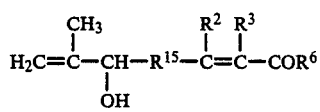

and acylating the hydroxyl group of this compound with, for example, a hydrocarbon carbonyl chloride.

Without resorting to the Wittig reaction, compounds of formula (I) in which $R^1$ has a triple bond as the unsaturated bond, $R^2$ is $OR^7$ and $R^7$ is a hydrogen or a hydrocarbon group can be produced, for example, by the following reaction in accordance with Tetrahedron Letters 15, 1491 (1972).

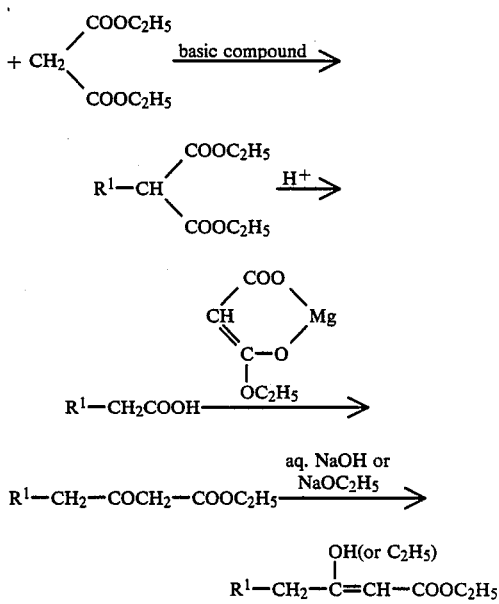

A general process for producing the beta,gamma-unsaturated carboxylic acids or their derivatives of formula (I)-b is based, for example, on the Wittig reaction between the carbonyl compounds of formula (II) given hereinabove and Wittig reagents of the following formula (IV)

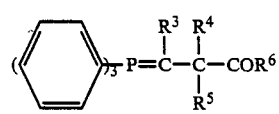 (IV)

wherein $R^3$, $R^4$, $R^5$ and $R^6$ are as defined above.

For example, compounds of formula (I)-b in which $R^5$ is the group $OR^7$ can be produced by subjecting a carbonyl compound of the following formula (V)

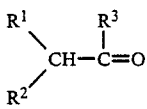

wherein $R^1$, $R^2$ and $R^3$ are as defined above,
and a compound of the following formula (VI)

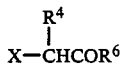

wherein $R^4$ and $R^6$ are as defined above and X represents a halogen atom such as Cl and Br,
to the Darzens condensation (see Organic Reactions Vol. 5, page 413) to form an epoxy compound represented by the following formula (VII)

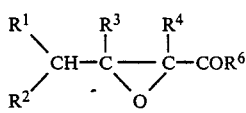

wherein $R^1$, $R^2$, $R^3$, $R^4$ and $R^6$ are as defined above, thermally decomposing the epoxy compound, for example by the method described in Agricultural Biological Chemistry 44 (11), 2709 (1980) to form a compound of the following formula

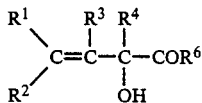

wherein $R^1$, $R^2$, $R^3$, $R^4$ and $R^5$ are as defined above, and acylating the hydroxyl group of this compound with, for example, a hydrocarbon carbonyl chloride.

Compounds of formula (I)-b in which $R^5$ is the group

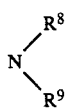

can be produced by nitrating a compound of the following formula (VIII)

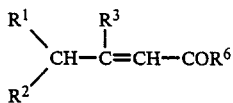

wherein $R^1$, $R^2$, $R^3$ and $R^6$ are as defined above,
to obtain a nitro compound of the following formula

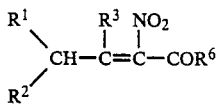

treating the nitro compound with potassium hydride and then with hydrochloric acid to form a beta,gamma-unsaturated carboxylic acid derivative of the following formula

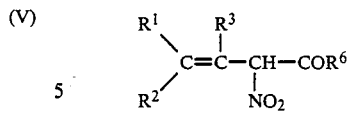

reducing the nitro group of the compound to form a compound of the following formula

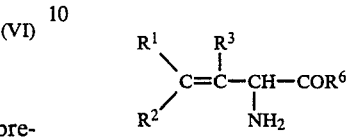

and acylating the amino group of the compound, for example, with a hydrocarbon carbonyl chloride.

Among the compounds of formula (I) used as an active ingredient in this invention, beta-alkynyl substituted alpha,beta-unsaturated carboxylic acids or their derivatives represented by the following formula (I)-a'

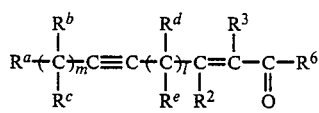

wherein $R^2$, $R^3$ and $R^6$ are as defined above, $R^a$ represents a group selected from the class consisting of a hydrogen atom, halogen atoms, a cyano group, a nitro group, groups $OR^7$, groups $SR^7$ and groups $NR^8R^9$ in which $R^7$, $R^8$ and $R^9$ are as defined above, $R^b$, $R^c$, $R^d$ and $R^e$ are identical or different and each represents an alkyl group having 1 to 7 carbon atoms or a group selected from the groups represented by $R^a$, m is an integer of 1 to 15, and l is 0 or an integer of 1 to 10 provided that the sum total of the number of carbon atoms +m+l+2 cannot exceed 15, and when l is 0, m is 1 and $R^3$ is a hydrogen atom, and that when m is an integer of 2 or more, $R^b$ groups and $R^c$ groups may respectively be identical or different, and likewise when l is an integer of at least 2, $R^d$ groups and $R^e$ groups may respectively be identical or different,
are novel compounds. Accordingly, these beta-alkynyl substituted alpha,beta-unsaturated carboxylic acids or their derivatives are also the subject matter claimed in this invention.

Compounds of general formula (I) including those of general formula (I)-a affect the metabolism of plants. For example, they inhibit the growth of certain types of plants, regulate the growth of certain types of plants, dwarf certain types of plants, or wither or kill certain types of plants.

The active compounds of formula (I) in accordance with this invention may be applied to seeds of plants, or to plants in various stages of growth.

The active compound in accordance with this invention, either as such or in the form of a composition, is applied in an amount sufficient for regulating plant metabolism to plants whose metabolism is desired to be regulated, seeds of such plants, a locus where such plants grow or to a locus where the growth of such plants is anticipated.

The active compound of this invention can regulate the metabolism of plants when applied in an amount of, for example, 10 kg to 20 kg, preferably 100 g to 10 kg, per hectare, When it is desired to inhibit the growth of undesirable plants or eradicate them by the active compound of this invention, the active compound, either as such or in the form of a composition, can be applied directly to plants or seeds or to the soil in a locus where beneficial plants or their seeds and undesirable plants or their seeds exist together or are likely to exist together in amounts sufficient to inhibit the growth of the undesirable plants or to eradicate them.

The undesirable plants may be defined as plants which grow in environments created by man such as paddies and upland farms after they have come into these environments from the surrounding nature and are recognized by man as being useless in these environments or doing damage to these environments. These undesirable plants include plants generally called weeds.

Examples of the weeds include plants of the family Gramineae such as those of the genera Digitaria, Sorghum and Echinochloa; plants of the family Plantaginaceae such as those of the genus Plantago; plants of the family Cyperaceae such as those of the genus Cyperus; plants of the family Compositae such as those of the genus Erigeron; plants of the family Cruciferae such as *Barbarae vulgaris* and those of the Genus Raphanus; plants of the family Solanaceae such as those of the genus Physalis; plants of the family Commelinaceae such as those of the genus Commelina; plants of the family Leguminosae such as those of the genus Medicago; plants of the family Polygonaceae such as *Polygonum hydropiper* L. and *Polygonum lapathifolium;* plants of the family Amaranthaceae such as *Amaranthus lividus* Loisel and Achyranthes fauriei Lev. et Van.; plants of the family Portalaceae such as *Portulaca oleracea* L.; and plants of the family Chenopodiaceae such as *Chenopodium album* L. and *Chenopodium album* L. var. centrorubrum Makino.

In the above case, the beneficial plants are, for example, plants which produce cereals, plants at least a part of which is useful as a feed, or lawn. The plants producing cereals are, for example, rice and corn. Examples of the plants at least a part of which is useful as a feed include potato, sweet potato, sugar cane, rye, barley and oats.

In some case, desirably, the active compound of this invention is applied while the undesirable plants do not grow to a large height, particularly while the undesirable plants do not become taller than the beneficial plants.

When it is desired to regulate the growth of plants by the active compound of this invention, it can be applied, either as such or in the form of a composition, to the plants, their seeds or to a locus where such plants are growing or their growth is anticipated in amounts sufficient to regulate the growth of the plants.

Suitable plants whose growth can be regulated by the active compound of this invention include, for example, the plants of the families Compositae, Chenopodiaceae, Polygonaceae and Partulacaceae.

To dwarf plants by the active compound of this invention, it can be applied, either as such or in the form of a composition, to plants to be dwarfed, their seeds, or a locus where such plants are growing or their growth is anticipated in amounts sufficient to drawf the plants.

Examples of suitable plants to be dwarfed by the active compound of this invention are plants of the families Compositae and Plantaginaceae.

The active compounds of this invention may be used in usual types of formulations such as solutions, emulsifiable concenrates, suspensions, dusts (powders), pastes or granules. These formulations may be prepared by using one or more of various adjuvants, for example, solid carriers such as talc, bentonite, clay kaolin, diatomaceous earth, white carbon, vermiculite, slaked lime, ammonium sulfate and urea; liquid carriers such as water, alcohols, dioxane, acetone, xylene, cyclohexane, methylnaphthalene and dimethylformamide; surface-active agents, emulsifiers, dispersants and spreaders such as alkyl sulfates, alkylsulfonic acid salts, ligninsulfonic acid salts, polyoxyethylene glycol ethers, polyoxyethylene alkylaryl ethers, polyoxyethylene sorbitan monoalkylates and dinaphthylmethanedisulfonic acid salts; and various other adjuvants such as carboxymethyl cellulose and gum arabic.

These formulations may be prepared, for example, by mixing the active compounds with a carrier and/or an emulsifier exemplified above.

The active compound of this invention can be present usually in an amount of 0.01 to 99% by weight, preferably 0.1 to 95% by weight, in such a formulation.

The active compound of this invention may be applied singly or as a mixture with another active compound or in each of the formulations exemplified above to plants by usual methods such as spraying, atomizing, scattering and dusting.

When the compound of this invention is used in the form of a formulation containing another active compound, known herbicides can be used as the other active compound, and also a synergist such as 3-amino-1,2,4-triazole can be used. It has been found that according to a formulation containing 3-amino-1,2,4-triazole together, the herbicidal activity of the active compound of this invention is increased and exhibited rapidly.

The active compound in accordance with this invention can be applied to annual and perennial broadleaved and narrow-leaved plants.

The following examples illustrate the present invention in more detail.

All parts in these examples are parts by weight unless otherwise specified. The herbicidal activity of each herbicide was evaluated on a scale of 0 to 5 unless otherwise specified. In this rating, "0" means that weeds were as alive as they had been before the application of the herbicide; "5" means that weeds entirely withered as a result of applying the herbicide; and 1,2,3 and 4 mean varying degrees of the weakened states of weeds between 0 and 5.

PRODUCTION EXAMPLES

Active compounds in accordance with this invention are produced by the methods described in the specification. The properties of these compounds are shown in Table 1.

TABLE 1

| Active compound No. | m.p. (° C.) | IR $\nu$max(cm$^{-1}$) | NMR Solvent | NMR $\delta$(ppm) | Mass M$^+$(m/e) |
|---|---|---|---|---|---|
| 138 | | 1760 1710 | CCl$_4$ | 7.4–6.5(5H) | |

TABLE 1-continued

| Active compound No. | m.p. (° C.) | IR νmax(cm$^{-1}$) | NMR Solvent | NMR δ(ppm) | Mass M$^+$(m/e) |
|---|---|---|---|---|---|
| | | 1630 | | 5.9(1H) 5.15(1H) 4.65(2H) 4.10(2H) 3.20(2H) 2.4–1.5(4H) 1.70(3H) 1.25(3H) 1.20(3H) | |
| 130 | | 3400–2600 1760 1710 1200 | CCl$_4$ | 9.33(1H) 7.33–6.63(4H) 5.76(1H) 5.13(1H) 4.87(2H) 4.60(2H) 2.20–1.80(2H) 1.67(3H) 1.77–1.0(5H) 0.90(3H) | |
| 136 | | 1760 1710 1630 1200 | CCl$_4$ | 7.67–6.50(4H) 6.25–5.50(3H) 4.63(2H) 4.30–3.95(4H) 2.20–1.30(4H) 1.27(3H) | |
| 140 | | 1760 1720 1650 1260 1190 | CCl$_4$ | 7.4–6.5(3H) 6.0–5.6(2H) 5.00(2H) 4.80(1H) 4.67(2H) 3.70(3H) 1.70(3H) | |
| 190 | | 1720 | CDCl$_3$ | 7.4–6.8(3H) 6.1–5.4(2H) 4.9(2H) 5.1–4.8(2H) 4.20(2H) 2.4–1.9(4H) 1.9–1.1(15H) | |
| 200 | | 1760 1710 1630 1270 1200 | CCl$_4$ | 7.5–6.6(4H) 5.95(1H) 5.70(1H) 5.20(1H) 5.0–4.8(2H) 4.66(2H) 4.10(2H) 2.4–1.5(4H) 1.85(3H) 1.70(3H) 1.25(3H) | |
| 202 | | 1760 1710 1630 1270 1180 | CCl$_4$ | 7.5–6.9(3H) 6.50(1H) 5.90(1H) 5.63(1H) 5.20(1H) 5.0–4.8(2H) 4.56(2H) 4.10(2H) 2.20(3H) 2.4–1.5(4H) 1.83(3H) 1.70(3H) 1.25(3H) | |
| 204 | | 1760 1710 1613 1270 1190 | CCl$_4$ | 7.4–6.9(3H) 6.50(1H) 5.90(1H) 5.66(1H) 5.3–5.0.(1H) 5.0–4.7(2H) 4.66(1H) 4.10(2H) 2.4–1.5(4H) 2.20(3H) 1.85(3H) 1.70(3H) 1.60(3H) 1.25(3H) | |
| 206 | | 1760 1710 1630 1270 1190 | CCl$_4$ | 7.5–6.6(4H) 5.95(1H) 5.70(1H) 5.20(1H) 5.0–4.8(2H) 4.66(2H) 3.60(3H) 2.4–1.5(4H) 1.85(3H) 1.70(3H) | |
| 208 | | 1760 1720 1640 1270 1180 | CCl$_4$ | 7.5–6.5(4H) 5.95(1H) 5.70(1H) 5.13(1H) 4.90(2H) 4.60–4.53(2H) 3.67(3H) 2.23(3H) 2.10–1.40(4H) 1.83(3H) 1.67(3H) | |
| 210 | | 3400–2600 1760 1710 1630 1200 | CDCl$_3$ | 7.33–6.67(4H) 6.20–5.83(3H) 5.17(1H) 4.93(2H) 4.67(2H) 2.30–1.65(4H) 1.67(6H) | |
| 218 | | 1760 1710 | CCl$_4$ | 7.70–6.67(4H) | |

TABLE 1-continued

| Active compound No. | m.p. (° C.) | IR νmax(cm⁻¹) | NMR Solvent | NMR δ(ppm) | Mass M⁺(m/e) |
|---|---|---|---|---|---|
| | | 1630 | | 6.03–5.57(2H) 5.53–5.07(1H) 4.93–4.53(2H) 4.63(2H) 4.23–4.00(1H) 3.67(3H) 1.86(3H) 1.67(3H) 1.60(3H) 2.33–0.90(8H) | |
| 220 | | 1720 | CCl₄ | 7.4–6.7(4H) 5.4–5.2(1H) 5.2–4.9(2H) 4.7(2H) 4.2(2H) 2.2–2.1(5H) 1.8(3H) 1.6(3H) 1.3(3H) | |
| 230 | | 3400 2200 1700 1620 | CDCl₃ | 6.83(1H) 6.20(1H) 4.43(2H) 4.23(2H) 3.24(1H) 1.27(3H) | 154 |
| 232 | | 2200 1710 1620 | CCl₄ | 6.73(1H) 6.17(1H) 4.18(2H) 4.08(2H) 1.26(3H) | 216 218 |
| 234 | 51–52 | 3400 2200 1720 1690 1620 | CDCl₃ | 6.76(1H) 6.13(1H) 4.41(2H) 3.76(3H) 2.89(1H) | 140 |
| 236 | 36–37 | 2200 1730 1620 | CCl₄ | 6.37(1H) 6.17(1H) 4.03(2H) 3.73(3H) | 204 202 |
| 238 | | 2200 1710 1620 | CCl₄ | 6.73(1H) 6.17(1H) 4.25(2H) 4.17(2H) 1.30(3H) | 160 158 |
| 240 | | 2200 1720 1620 | CCl₄ | 6.71(1H) 6.13(1H) 4.21(2H) 3.69(3H) | 160 158 |
| 242 | | 2300–3500 2200 1700 1620 | CDCl₃ | 8.79(1H) 6.89(1H) 6.20(1H) 4.28(2H) | |
| 252 | | 3300 2200 1660 1610 1550 | CDCl₃ | 6.73(1H) 6.13(1H) 5.30–5.60(1H) 4.05(2H) 4.00(1H) 1.23(3H) 1.13(3H) | 229 231 |
| 254 | | 3400 2200 1710 1590 | CCl₄ | 7.30(1H) 4.48(1H) 4.28(2H) 3.59(1H) 1.36(3H) | 232 234 |
| 256 | | 3400 2200 1720 1590 | CCl₄ | 6.96(1H) 4.46(2H) 4.26(2H) 3.59(1H) 1.33(3H) | 188 190 |
| 258 | | 2200 1720 1590 | CCl₄ | 7.28(1H) 4.28(2H) 4.08(2H) 1.33(3H) | 298 296 294 |
| 260 | | 2200 1720 1590 | CCl₄ | 7.28(1H) 4.31(2H) 4.25(2H) 1.35(3H) | 254 252 250 |
| 262 | | 2200 1720 1595 | CCl₄ | 6.92(1H) 4.25(2H) 4.10(2H) 1.33(3H) | 254 252 250 |
| 264 | | 2200 1720 1595 | CCl₄ | 6.92(1H) 7.31(2H) 4.28(2H) 1.36(3H) | 210 208 206 |
| 266 | | 3500 2200 1710 1585 | CCl₄ | 7.26(1H) 4.43(2H) 3.83(3H) 3.36(1H) | 220 218 |
| 268 | 50–51 | 3500 2200 1715 1690 1590 | CDCl₃ | 6.92(1H) 4.46(2H) 3.86(3H) 2.53(1H) | 176 174 |
| 270 | | 2200 1720 1590 | CCl₄ | 7.30(1H) 4.10(2H) 3.83(3H) | 284 282 280 |
| 272 | | 2200 1725 1590 | CCl₄ | 7.31(1H) 4.36(2H) 3.83(3H) | 240 238 236 |
| 274 | | 2200 1725 1600 | CCl₄ | 6.89(1H) 4.08(2H) 3.79(3H) | 240 238 236 |
| 276 | | 2200 1730 1590 | CCl₄ | 7.18(1H) 4.86(1H) 4.53(2H) 4.33(2H) 3.59(2H) 1.66(6H) 1.40(3H) | |
| 278 | | 3400 2200 1730 1590 | CDCl₃ | 7.17(1H) 4.48(2H) 4.07(2H) 3.00(1H) 1.33(3H) | |
| 280 | 53–55 | 2200 1725 1590 | CCl₄ | 7.26(1H) 4.33(2H) 4.18(2H) 1.40(3H) | 243 241 |
| 282 | | | CDCl₃ | 6.72(1H) 6.13(1H) | |

TABLE 1-continued

| Active compound No. | m.p. (° C.) | IR νmax(cm⁻¹) | NMR Solvent | δ(ppm) | Mass M⁺(m/e) |
|---|---|---|---|---|---|
| | | | | 4.7–4.9(1H) | |
| | | | | 4.36(2H) | |
| | | | | 3.9–4.3(4H) | |
| | | | | 1.1–1.9(18H) | |
| | | | | 0.9(3H) | |
| 284 | | | CDCl₃ | 6.70(1H) 6.13(1H) | |
| | | | | 4.40(2H) | |
| | | | | 3.5–3.9(1H) | |
| | | | | 4.12(2H) | |
| | | | | 1.0–2.0(12H) | |
| | | | | 0.9(3H) | |
| 286 | | 2200 1715 | CCl₄ | 6.75(1H) 6.20(1H) | |
| | | | | 4.0–4.3(4H) | |
| | | | | 1.0–1.9(12H) | |
| | | | | 0.9(3H) | |
| 288 | | 2200 1750 1710 | CCl₄ | 6.65(1H) 4.10(2H) | |
| | | | | 6.10(1H) 2.00(3H) | |
| | | | | 4.70(2H) 1.25(3H) | |
| 290 | | 2200 1720 1615 | CCl₄ | 7.9–8.2(2H) | |
| | | | | 7.3–7.6(3H) | |
| | | | | 6.75(1H) 6.15(1H) | |
| | | | | 5.02(2H) 4.15(2H) | |
| | | | | 1.26(3H) | |
| 292 | | 2200 1715 | CCl₄ | 6.70(1H) 6.22(1H) | |
| | | | | 4.96(2H) 4.18(2H) | |
| | | | | 3.05(3H) 1.30(3H) | |
| 294 | | 2200 1710 | CCl₄ | 7.34(1H) 6.95(1H) | |
| | | | | 6.62–6.80(2H) | |
| | | | | 6.20(1H) 4.92(2H) | |
| | | | | 4.20(2H) 1.25(3H) | |
| 296 | | 2200 1708 | CCl₄ | 7.35(1H) | |
| | | | | 6.8–7.1(6H) | |
| | | | | 6.72(1H) 6.13(1H) | |
| | | | | 4.83(1H) 4.20(2H) | |
| | | | | 1.26(3H) | |
| 298 | | 2200 1710 | CCl₄ | 7.05–7.30(5H) | |
| | | | | 6.70–7.00(4H) | |
| | | | | 6.72(1H) 6.06(1H) | |
| | | | | 4.90(2H) 4.65(2H) | |
| | | | | 4.10(2H) 1.22(3H) | |
| 300 | | 2200 1720 1620 | CCl₄ | 6.76(1H) 6.16(1H) | |
| | | | | 4.9–4.7(1H) | |
| | | | | 4.33(2H) 4.20(2H) | |
| | | | | 3.8–3.2(10H) | |
| | | | | 1.8–1.1(6H) | |
| | | | | 1.16(3H) | |
| 302 | | 2200 1720 1620 | CCl₄ | 6.73(1H) 6.13(1H) | |
| | | | | 4.31(2H) 4.20(2H) | |
| | | | | 3.75–3.30(8H) | |
| | | | | 3.10(1H) 1.16(3H) | |
| 304 | | 2200 1720 1620 | CCl₄ | 6.75(1H) 6.20(1H) | |
| | | | | 4.3–4.0(2H) | |
| | | | | 4.03(2H) | |
| | | | | 3.75–3.30(8H) | |
| | | | | 1.16(3H) | |
| 306 | | 2200 1620 1745 1710 | CCl₄ | 7.35–6.95(2H) | |
| | | | | 6.70(1H) 6.67(1H) | |
| | | | | 6.15(1H) 4.85(2H) | |
| | | | | 4.65(2H) 4.15(2H) | |
| | | | | 1.27(3H) | |
| 308 | | 2200 1765 1715 1620 | CCl₄ | 7.45–7.0(2H) | |
| | | | | 6.75(1H) 6.73(1H) | |
| | | | | 4.90(2H) 4.66(2H) | |
| | | | | 4.23(2H) | |
| | | | | 3.80–3.25(8H) | |
| | | | | 1.15(3H) | |
| 310 | | 2200 1765 1710 1620 | CCl₄ | 7.10–6.80(2H) | |
| | | | | 6.50(1H) 6.70(1H) | |
| | | | | 6.13(1H) 4.90(2H) | |
| | | | | 4.60(2H) 4.20(2H) | |
| | | | | 2.25(3H) 1.30(3H) | |
| 312 | | 3150 1760 1705 1620 | CDCl₃ | 7.45(1H) 6.95(1H) | |
| | | | | 6.75(1H) 6.20(1H) | |
| | | | | 5.00(2H) 4.75(2H) | |
| | | | | 4.20(2H) 1.90(3H) | |
| 314 | | 2200 1760 1715 1620 | CCl₄ | 7.10–6.80(2H) | |
| | | | | 6.73(1H) 6.63(1H) | |
| | | | | 6.07(1H) 4.85(2H) | |
| | | | | 4.65(1H) 4.13(2H) | |
| | | | | 2.25(3H) 1.67(3H) | |

TABLE 1-continued

| Active compound No. | m.p. (° C.) | IR $\nu$max(cm$^{-1}$) | NMR Solvent | NMR $\delta$(ppm) | Mass M$^+$(m/e) |
|---|---|---|---|---|---|
| 316 | | 2200 1760<br>1710 1620 | CCl$_4$ | 1.25(3H)<br>7.80–6.85(7H)<br>6.63(1H) 6.07(1H)<br>4.85(2H) 4.65(2H)<br>4.13(2H) 1.25(3H) | |
| 318 | | 2200 1760<br>1720 1620 | CCl$_4$ | 7.30(1H)<br>7.1–6.7(6H)<br>6.15(1H) 4.90(2H)<br>4.65(1H) 4.20(2H)<br>1.65(3H) 1.26(3H) | |
| 320 | | 2200 1765<br>1715 1620 | CCl$_4$ | 7.10–6.85(2H)<br>6.70(1H) 6.50(1H)<br>6.20(1H) 4.90(2H)<br>4.60(2H) 4.25(2H)<br>3.75–3.20(8H)<br>2.25(3H) 1.15(3H) | |
| 322 | | 2200 1765<br>1715 1620 | CCl$_4$ | 7.37(1H) 6.85(1H)<br>6.67(1H) 6.13(1H)<br>4.90(2H) 4.60(2H)<br>4.16(2H)<br>3.70–3.20(8H)<br>1.15(3H) | |
| 324 | | 2200 1760<br>1720 1620 | CCl$_4$ | 7.10–6.80(2H)<br>6.73(1H) 6.53(1H)<br>6.17(1H) 4.80(2H)<br>4.67(1H) 4.20(2H)<br>3.75–3.20(8H)<br>2.23(3H) 1.67(3H)<br>1.15(3H) | |
| 326 | | 2200 1760<br>1710 1620 | CCl$_4$ | 7.45–6.65(6H)<br>6.60(1H) 6.10(1H)<br>4.90(2H) 4.60(2H)<br>4.45(2H) 4.10(2H) | |
| 328 | | 3400 1690<br>1580 | CDCl$_3$ | 9.9–9.5(1H)<br>7.90(1H)<br>7.65–7.00(6H)<br>6.95(1H) 4.70(2H)<br>3.00(2H) | |
| 330 | | 2200 1760<br>1710 1620 | CCl$_4$ | 7.33–6.95(2H)<br>6.70(1H) 6.62(1H)<br>6.02(1H) 4.58(2H)<br>4.20(2H) 4.10(2H)<br>2.40(2H) 1.90(2H)<br>1.23(3H) | |
| 334 | | 1760 1640 | CCl$_4$ | 7.4–6.7(3H)<br>6.6(2H) 4.9(2H)<br>4.7(2H) 3.4(4H)<br>1.2(6H) | |
| 336 | | 1760 1640 | CDCl$_3$ | 7.4–6.6(5H)<br>4.95(2H) 4.7(2H)<br>4.2–3.8(2H)<br>3.1–2.7(1H)<br>2.0–1.0(6H)<br>1.2(3H) | |
| 338 | | 1760 1720 | CCl$_4$ | 7.5–6.5(4H)<br>6.2(1H) 4.7(2H)<br>4.6(2H) 4.1(2H)<br>2.0–1.1(2H)<br>1.1–0.8(3H) | |
| 340 | | 1760 1710 | CCl$_4$ | 7.4–6.7(3H)<br>6.6(1H) 4.95(2H)<br>4.7(2H) 4.2(2H)<br>2.05(3H) 1.3(3H) | |
| 366 | | 1750 1480<br>1180 | CCl$_4$ | 7.33(1H) 7.16(1H)<br>6.83(1H) 5.33(1H)<br>5.10(2H) 4.73(2H)<br>4.20(2H) 1.75(3H)<br>1.25(3H) | |
| 368 | | 1750 1490<br>1180 | CCl$_4$ | 7.07–6.50(3H) 5.33(1H)<br>5.10(2H) 4.67(2H)<br>4.17(2H) 2.23(3H)<br>1.77(3H) 1.23(3H) | |
| 370 | | 3400–2600<br>1760 1740<br>1190 | CCl$_4$ | 10.47(1H)<br>7.27–6.63(3H)<br>5.43(1H) 5.17(2H)<br>4.73(2H) 1.80(3H) | |
| 376 | | 3200 1750<br>1670 1580<br>1200 | CCl$_4$ | 7.8–7.1(5H)<br>7.0–6.7(2H)<br>5.56(1H) 5.13(2H)<br>4.80(2H) 1.80(3H) | |

TABLE 1-continued

| Active compound No. | m.p. (° C.) | IR vmax(cm$^{-1}$) | NMR Solvent | NMR δ(ppm) | Mass M$^+$(m/e) |
|---|---|---|---|---|---|
| 377 | | 3370 1720 1660 | CDCl$_3$ | 7.50–7.83(1H) 6.67–7.37(3H) 5.00–5.10(2H) 5.07(1H) 4.50(2H) 3.73(3H) 1.80(3H) | |
| 378 | | 1750 | CCl$_4$ | 6.70–7.30(3H) 5.30(1H) 5.07(2H) 4.70(2H) 4.07(2H) 1.73(3H) 1.00–1.60(16H) 0.87(3H) | |
| 380 | | 3400–3550 1750 1620 | CCl$_4$ | 6.83–7.30(3H) 5.50(1H) 5.10(2H) 4.73(2H) 2.97–3.53(4H) 1.76(3H) 1.00–1.33(6H) | |
| 394 | | 1750 1590 1330 1180 | CCl$_4$ | 6.96–7.40(4H) 5.33(1H) 5.00–5.13(2H) 4.70(2H) 4.17(2H) 1.73(3H) 1.27(3H) | |
| 396 | | 1740 | CCl$_4$ | 7.75–6.8(7H) 5.1–4.6(3H) 4.15(2H) 2.20(1H) 1.70(3H) 1.65(3H) 1.20(3H) | |
| 414 | | 1740 1635 | CCl$_4$ | 7.4–6.7(3H) 6.0–5.4(1H) 5.4–4.7(3H) 4.7(2H) 4.15(2H) 3.0–2.6(2H) 2.1(1H) 1.6(3H) 1.3(3H) | |
| 416 | | 1740 | | 6.70–7.40(3H) 4.75–5.55(4H) 4.70(2H) 3.70(3H) 2.50–2.75(2H), 1.75–2.25(4H) 1.50–1.70(12H) | |

FORMULATION EXAMPLE 1

One part of active compound No. 366 in accordance with this invention was added to 5000 parts of a mixture of acetone and water (in a volume ratio of 1:1), and 2.6 parts of a nonionic surfactant (Sorpol 2680, a trade name) was added to form a solution.

FORMULATION EXAMPLE 2

One part of active compound No. 232 in accordance with this invention was added to a mixture of 10,000 parts of water and 4 parts of acetone, and 1.6 parts of a non-ionic surfactant (Sorpol 2680, a trade name) was added to form a solution.

FORMULATION EXAMPLE 3

A mixture of active compound No. 230 in accordance with this invention (0.8 part), 0.63 part of a xylene/isophorone mixture, and 0.07 part of a nonionic surfactant (Sorpol 800-A, a trade name) was diluted with water to a predetermined concentration.

FORMULATION EXAMPLE 4

A mixture of active compound No. 100 in accordance with this invention (0.1 part), 0.03 part of bentonite, and 0.03 part of a nonionic surfactant (Sorpol 800-A, a trade name) was fully mixed to form a wettable powder. It was diluted with water to a predetermined concentration.

EXAMPLE 1

Active compounds of this invention were formulated in accordance with Formulation Examples given hereinabove.

Seeds of plants were sown, and after germination, grown for 2 to 3 weeks.

A formulation of each of the active compounds was applied to these plants at a rate of about 0.1 g/m$^2$ of the active compound. Thereafter, without further applying the formulation, the plants were grown for 2 weeks. The results are shown in Table 2.

In Table 2 and subsequent tables, the plants were indicated by the following numbers.

(1) *Erigeron annuus*
(2) *Digitaria sanquinalis*
(3) *Plantago asiatica*
(4) *Cyperus rotundus*
(5) *Polygonum hydropiper*
(6) *Polygonum lapathifoliam*
(7) *Chenopodium album* L. var. centrorubrum Makino
(8) *Chenopodium album* L.
(9) *Amaranthus lividus*
(10) *Portulaca oleracea*
(11) rice
(12) corn

*Erigeron annuus* is an annual broad-leaved plant. *Digitaria sanquinalis* is an annual narrow-leaved plant. *Plantago asiatica* is a perennial broad-leaved plant. *Cyperus*

*rotundus* is a perennial narrow-leaved plant. The other plants (5) to (10) are annual broad-leaved plants.

As is clear from the results given in Table 2, the active compounds shown in Table 2 in accordance with this invention have excellent herbicidal activity against the weeds, but are non-toxic to rice and corn.

TABLE 2

| Acid compound No. | Herbicidal activity | | | | | | | | | | | |
|---|---|---|---|---|---|---|---|---|---|---|---|---|
| | (1) | (2) | (3) | (4) | (5) | (6) | (7) | (8) | (9) | (10) | (11) | (12) |
| 366 | 5 | 2 | 4 | 4 | 3 | 5 | 5 | 5 | 5 | 5 | 0 | 0 |
| 370 | 5 | 2 | 4 | 4 | 5 | 5 | 5 | 4 | 5 | 5 | 0 | 0 |
| 376 | 5 | 1 | 3 | 4 | 2 | 3 | 4 | 4 | 5 | 3 | 0 | 0 |
| 368 | 4 | 1 | 2 | 3 | 2 | 5 | 4 | 5 | 5 | 5 | 1 | 0 |
| 206 | 5 | 2 | 4 | 3 | 3 | 2 | 5 | 5 | 5 | 2 | 1 | 0 |
| 136 | 5 | 2 | 5 | 2 | 5 | 1 | 5 | 5 | 5 | 3 | 1 | 0 |
| 208 | 5 | 2 | 3 | 3 | 2 | 2 | 5 | 5 | 3 | 5 | 1 | 0 |
| 140 | 5 | 1 | 4 | 4 | 4 | 2 | 5 | 4 | 5 | 4 | 0 | 0 |
| 200 | 5 | 1 | 5 | 2 | 3 | 5 | 5 | 5 | 5 | 4 | 1 | 0 |
| 210 | 5 | 1 | 3 | 2 | 2 | 2 | 5 | 5 | 5 | 5 | 0 | 0 |
| 202 | 4 | 1 | 4 | 1 | 2 | 2 | 5 | 5 | 5 | 5 | 0 | 0 |
| 306 | 5 | 3 | 4 | 3 | 1 | 1 | 5 | 5 | 5 | 4 | 0 | 1 |
| 312 | 5 | 2 | 3 | 2 | 1 | 1 | 5 | 5 | 5 | 3 | 0 | 0 |
| 308 | 5 | 2 | 3 | 3 | 1 | 1 | 4 | 5 | 5 | 3 | 0 | 0 |
| 310 | 5 | 2 | 4 | 2 | 5 | 4 | 5 | 5 | 5 | 5 | 1 | 0 |
| 316 | 3 | 1 | 3 | 1 | 1 | 1 | 5 | 5 | 3 | 2 | 0 | 0 |
| 328 | 4 | 2 | 2 | 1 | 2 | 2 | 4 | 4 | 2 | 2 | 0 | 0 |
| 330 | 4 | 2 | 3 | 3 | 1 | 1 | 4 | 5 | 5 | 3 | 0 | 0 |
| 372 | 4 | 1 | 3 | 3 | 3 | 3 | 5 | 5 | 5 | 4 | 0 | 0 |
| 374 | 4 | 1 | 3 | 3 | 3 | 3 | 5 | 5 | 5 | 4 | 0 | 0 |
| 212 | 4 | 1 | 1 | 1 | 2 | 2 | 5 | 5 | 5 | 3 | 0 | 0 |
| 214 | 4 | 1 | 3 | 1 | 2 | 2 | 5 | 5 | 5 | 3 | 0 | 0 |
| 138 | 5 | 1 | 3 | 1 | 3 | 3 | 5 | 5 | 5 | 4 | 0 | 0 |
| 130 | 5 | 2 | 5 | 2 | 4 | 4 | 5 | 5 | 5 | 5 | 0 | 0 |
| 132 | 4 | 2 | 4 | 3 | 3 | 3 | 5 | 5 | 5 | 4 | 0 | 0 |
| 134 | 5 | 1 | 4 | 2 | 3 | 3 | 5 | 5 | 5 | 4 | 1 | 0 |
| 377 | 2 | 1 | 2 | 1 | 3 | 3 | 5 | 5 | 5 | 4 | 0 | 0 |
| 378 | 4 | 1 | 3 | 1 | 4 | 3 | 5 | 5 | 5 | 3 | 1 | 0 |
| 380 | 5 | 1 | 4 | 1 | 4 | 3 | 5 | 5 | 5 | 4 | 0 | 0 |
| 394 | 2 | 1 | 2 | 1 | 2 | 2 | 5 | 5 | 4 | 2 | 0 | 0 |
| 396 | 4 | 1 | 2 | 2 | 2 | 2 | 4 | 4 | 3 | 2 | 0 | 0 |
| 414 | 4 | 2 | 4 | 1 | 3 | 3 | 5 | 5 | 4 | 3 | 0 | 0 |
| 338 | 4 | 1 | 3 | 1 | 4 | 4 | 5 | 5 | 5 | 4 | 1 | 0 |
| 334 | 4 | 1 | 4 | 3 | 4 | 4 | 5 | 5 | 5 | 3 | 0 | 0 |
| 336 | 5 | 1 | 4 | 4 | 4 | 4 | 5 | 5 | 5 | 3 | 0 | 0 |
| 340 | 5 | 3 | 4 | 2 | 4 | 4 | 5 | 5 | 5 | 4 | 0 | 0 |
| 218 | 3 | 1 | 3 | 1 | 2 | 2 | 5 | 5 | 3 | 2 | 0 | 0 |
| 220 | 4 | 1 | 3 | 1 | 4 | 3 | 5 | 5 | 5 | 3 | 0 | 0 |
| 416 | 4 | 1 | 4 | 2 | 4 | 4 | 5 | 5 | 5 | 3 | 0 | 0 |
| 190 | 4 | 2 | 4 | 1 | 4 | 4 | 5 | 5 | 4 | 4 | 1 | 0 |

EXAMPLE 2

In the same way as in Example 1, each of the active compounds indicated in Table 3 was tested except that the total amount of each active compound applied became about 0.5 g/m². The results are shown in Table 3. It is seen from Table 3 that these active compounds show excellent herbicidal activity against any of the weeds tested.

TABLE 3

| Acid compound No. | Herbicidal activity | | | |
|---|---|---|---|---|
| | (1) | (2) | (3) | (4) |
| 306 | 5 | 4 | 5 | 5 |
| 308 | 5 | 4 | 5 | 5 |
| 312 | 5 | 4 | 4 | 4 |
| 320 | 5 | 4 | 4 | 4 |
| 324 | 4 | 5 | 4 | 4 |
| 326 | 5 | 4 | 4 | 3 |
| 310 | 5 | 3 | 4 | 4 |
| 314 | 3 | 5 | 5 | 4 |
| 322 | 4 | 4 | 4 | 4 |
| 316 | 4 | 3 | 3 | 3 |
| 318 | 3 | 3 | 1 | 1 |
| 328 | 3 | 1 | 3 | 2 |
| 306(*) | 5 | 3 | 4 | 5 |
| 308(*) | 5 | 3 | 5 | 5 |
| 330(*) | 5 | 2 | 5 | 4 |
| 366 | 5 | 4 | 5 | 5 |
| 368 | 5 | 4 | 5 | 5 |
| 370 | 5 | 3 | 5 | 5 |
| 376 | 5 | 2 | 3 | 4 |
| 130 | 5 | 4 | 5 | 5 |
| 200 | 5 | 3 | 5 | 3 |
| 202 | 5 | 2 | 5 | 4 |
| 206 | 5 | 2 | 5 | 4 |
| 208 | 5 | 3 | 4 | 4 |
| 210 | 5 | 2 | 4 | 4 |
| 138 | 5 | 2 | 4 | 3 |
| 136 | 5 | 3 | 5 | 4 |
| 204 | 3 | 2 | 3 | 2 |

The asterisks in the table show that the total amount of the active compound was about 0.25 g/m².

EXAMPLE 3

Each of the active compounds indicated in Table 4 was tested as in Example 1 except that the total amount of each active compound applied was about 0.5 to 1.0 g/m². The degree of withering of the weeds examined seven days after the application is shown in Table 4. The degree of withering in Table 4 was rated by a scale of 1 to 5 in which 1 means that the weeds remained nearly as alive as before the application, 5 means that the weeds are entirely withered, and 2, 3 and 4 are varying degrees of withering obtained by dividing the scale between 1 and 5 into four equal parts.

TABLE 4

| Acid compound No. | Herbicidal activity | | | |
|---|---|---|---|---|
| | (1) | (2) | (3) | (4) |
| 100(*) | 5 | 5 | 5 | 5 |
| 232 | 5 | 5 | 4 | 2 |
| 236 | 5 | 5 | 4 | 2 |
| 258 | 5 | 5 | 4 | 2 |
| 262 | 5 | 5 | 4 | 2 |
| 270 | 5 | 5 | 4 | 3 |
| 274 | 5 | 5 | 4 | 4 |
| 292 | 5 | 5 | 2 | 2 |
| 304 | 5 | 5 | 3 | 2 |
| 240 | 4 | 5 | 2 | 2 |
| 266 | 4 | 5 | 2 | 2 |
| 268 | 4 | 5 | 2 | 2 |
| 278 | 4 | 5 | 2 | 2 |
| 280 | 4 | 5 | 4 | 3 |
| 238 | 3 | 4 | 2 | 2 |
| 254 | 3 | 4 | 2 | 2 |
| 256 | 3 | 4 | 2 | 2 |
| 260 | 3 | 4 | 2 | 2 |
| 264 | 3 | 4 | 2 | 2 |
| 272 | 3 | 4 | 2 | 2 |
| 284 | 2 | 5 | 2 | 2 |
| 286 | 2 | 5 | 2 | 2 |
| 252 | 3 | 3 | 2 | 2 |
| 282 | 2 | 4 | 2 | 2 |
| 290 | 2 | 4 | 2 | 2 |

The asterisk in the table shows that the amount of the active compound was about 2.0 g/m², and the the degree of withering was examined 3 days after application.

EXAMPLE 4

To 0.008 part by volume of acetone and 0.0032 part of Sorpol 2680 (a trade name) was added 0.002 part of each of active compounds Nos. 232 and 258, and the mixture was diluted with 20 parts of water.

Soil was filled in pots each having a diameter of 10 cm and a depth of 10 cm, and seeds of *Erigeron annuus* and *Plantago asiatica* were sown. The seeds were then covered with soil, and each dilution prepared as above was applied to the surface of the soil in such an amount that the amount of the active compound corresponded to 0.25 g/m². The number of buds from the seeds and the state of growth were observed. With any of the active compounds tested, none of the seeds of these weeds germinated, and they showed a complete effect of inhibiting germination.

EXAMPLE 5

Each of active compounds Nos. 200, 306, and 366 (0.038 part) was added to a mixture of 300 parts of water and 300 parts of acetone, and 0.3 part of Sorpol 2680 (trade name) was added as a spreader. The mixture was sprayed onto the leaves and stalks of *Erigeron annuus, Polygonum hydropiper, Portulaca oleracea* and *Amaranthus lividus* having a height of about 40 cm in an amount, as the active compound, of 0.025 g/m². The the plants were further grown, and the state of growth was visually observed. With any of these active compounds, the height of these weeds after 30 days remained at 40 cm which was their height at the time of spraying the active compounds. In *Erigeron annuus*, many axillary buds occurred. In a non-treated area, the weeds grew taller than they were at the time of spraying, and after the lapse of 30 days, *Erigeron annuus* grew to a height of about 100 cm; *Polygonum hydropiper*, to a height of about 8 cm; *Portulaca oleracea*, to a height of about 80 cm; and *Amaranthus lividus*, to a height of about 70 cm.

What we claim is:

1. A plant metabolism regulating agent comprising an active ingredient in an amount effective to regulate plant metabolism and an inert carrier, said active ingredient being a compound represented by the formula (I) below

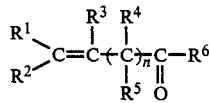

wherein $R^1$ represents a hydrogen atom or a linear or branched aliphatic hydrocarbon group which has 1 to 5 unsaturated bonds selected from carbon-carbon double and triple bonds and in which the main chain has 2 to 15 carbon atoms;

wherein said aliphatic hydrocarbon group may be substituted by at least one substituent selected from the group consisting of a halogen atom, a cyano group, a nitro group, an epoxy group, a tetrahydropyranyloxy group, a cycloalkyl or cycloalkenyl group having 5 to 7 carbon atoms as ring members and the group $-OR^{11}$, wherein $R^{11}$ represents a hydrogen atom, a hydrocarbon group having 1 to 15 carbon atoms or a hydrocarbon-carbonyl group having 2 to 16 carbon atoms, wherein the hydrocarbon group or moiety for $R^{11}$ may be substituted by a substituent selected from the group consisting of alkyl groups having 1 to 7 carbon atoms, alkenyl groups having 2 to 7 carbon atoms, cycloalkyl or cycloalkenyl groups having 5 to 7 carbon atoms as ring members, a phenoxy group, an unsubstituted naphthoxy group and a pyridyloxy group, wherein the phenoxy group and the pyridyloxy group as the substituent of said hydrocarbon group or moiety may be substituted by a halogen atom, a cyano group, a nitro group, an unsubstituted or halogen-substituted alkyl group having 1 to 4 carbon atoms or the group $OR^{11}$;

$R^2$ represents a group selected from the group consisting of a hydrogen atom, halogen atom, a cyano group, a nitro group, an alkenyl or alkynyl group having 2 to 7 carbon atoms which may be substituted by said substituent for the hydrocarbon group or moiety for $R^{11}$, a cycloalkyl or cycloalkenyl group which has 3 to 7 carbon atoms as ring members and may be substituted by said substituent for the hydrocarbon group or moiety for $R^{11}$, or a phenyl group which may be substituted by said substituent for the hydrocarbon group or moiety for $R^{11}$, and groups $OR^7$, in which $R^7$ represents a hydrogen atom, a hydrocarbon group having 1 to 15 carbon atoms, a hydrocarbon-carbonyl group having 2 to 16 carbon atoms, a hydrocarbon-sulfonyl group having 1 to 15 carbon atoms or the group $HSO_2-$, wherein the hydrocarbon group or moiety for $R^7$ may be substituted by said substituent for the hydrocarbon group or moiety for $R^{11}$;

$R^3$ represents a group selected from said groups represented by $R^2$;

$R^4$ and $R^5$ are identical or different and each represents a group selected from said groups represented by $R^2$;

$R^6$ represents a group selected from the group consisting of groups $OR^{10}$ and groups $NR^8R^9$, in which $R^{10}$ represents a hydrogen atom, one equivalent of a cation, or a hydrocarbon group having 1 to 15 carbon atoms which may be interrupted by an oxygen atom and $R^8$ and $R^9$ are identical or different, and each represents a hydrogen atom, a hydrocarbon group having 1 to 10 carbon atoms, a hydrocarbon-carbonyl group having 2 to 10 carbon atoms or a hydrocarbon-sulfonyl group having 1 to 10 carbon atoms, or $R^8$ and $R^9$ together may form a saturated, 5 to 6-membered ring containing, as a single heteroatom, the nitrogen atom to which they are bonded, wherein said one equivalent of a cation is selected from the group consisting of an alkali metal cation, one half of an alkaline earth metal cation and a primary, secondary, tertiary or quaternary ammonium cation of $NH_4^+$ (in which R's are identical or different and each represents a hydrogen atom, an alkyl group having 1 to 6 carbon atoms, a phenyl group or a benzyl group), and said hydrocarbon group for $R^{10}$, $R^8$ and $R^9$ may be substituted by said substituent for the hydrocarbon group or moiety for $R^{11}$; and n is 0 or 1 provided that (1) in the case of n=0, $R^1$ cannot be a hydrogen atom or a methyl group and when $R^1$ has as the unsaturated bond a double bond conjugated with the double bond between the carbon atoms to which $R^1$ and $R^3$ are bonded, the number of carbon atoms of the main chain of $R^1$ cannot be more than 4, and (2) in the case of n=1, when $R^1$, $R^2$ and $R^4$ are hydrogen atoms at the same time, $R^5$ cannot be a hydrogen atom or an unsubstituted hydrocarbon group having 1 to 15 carbon atoms, and when $R^1$ is a hydrogen atom and $R^2$ is an alkyl group having 1 to 2 carbon atoms, $R^4$ cannot be a hydrogen atom or an alkyl group having 1 to 2 carbon atoms.

however, at least one of $R^1$, $R^2$, $R^3$, $R^4$ and $R^5$ is a hydrocarbon group or moiety substituted by a phenoxy group or an unsubstituted naphthoxy group or a group having such a hydrocarbon group or moiety.

2. The plant metabolism regulating agent of claim 1 wherein the optionally substituted aliphatic hydrocarbon group represented by $R^1$ in formula (I) has 2 to 13 carbon atoms in the main chain.

3. The plant metabolism regulating agent of claim 1 wherein the optionally substituted aliphatic hydrocarbon group represented by $R^1$ in formula (I) has at least one carbon-carbon unsaturated bond in the main chain.

4. The plant metabolism regulating agent of claim 1 wherein the group $R^7$ of $OR^7$ represented by $R^2$, $R^3$, $R^4$ or $R^5$ in formula (I) is an aliphatic hydrocarbon-carbonyl group having 2 to 16 carbon atoms which may be substituted, a benzoyl group, a naphthylcarbonyl group, an alkyl group having 1 to 15 carbon atoms, alkenyl group having 2 to 15 carbon atoms, a cycloalkyl or cycloalkenyl group having 5 to 7 carbon atoms as ring members, a phenyl group, a naphthyl group, an alkylsulfonyl group having 1 to 15 carbon atoms, a phenylsulfonyl group or a naphthylsulfonyl group.

5. The plant metabolism regulating agent of claim 1 wherein groups $R^8$ and $R^9$ of the group $NR^8R^9$ represented by $R^6$ in formula (I) are identical or different, and each represents an alkyl group having 1 to 10 carbon atoms which may be substituted, a cycloalkyl or cycloalkenyl group having 5 to 7 carbon atoms as ring members, a phenyl group, a naphthyl group, an alkylcarbonyl group having 2 to 10 carbon atoms, a benzoyl group or a naphthoyl group.

6. The plant metabolism regulating agent of claim 1 wherein group $R^{10}$ of $OR^{10}$ represented by $R^6$ in formula (I) represents an alkali metal cation, an alkaline metal cation, a primary, secondary, tertiary or quaternary ammonium cation, an alkyl group having 1 to 15 carbon atoms, an alkyl group having 4 to 15 carbon atoms which is interrupted by an oxygen atom, an alkenyl or alkynyl group having 2 to 15 carbon atoms, a cycloalkyl or cycloalkenyl group having 5 to 7 carbon atoms as ring members, a phenyl group, or naphthyl group.

7. The plant metabolism regulating agent of claim 1 wherein n in formula (I) is 0.

8. The plant metabolism regulating agent of claim 1 wherein n in formula (I) is 1.

9. The plant metabolism regulating agent of claim 1 wherein the optionally substituted aliphatic hydrocarbon group represented by $R^1$ is substituted by a substituent selected from the class consisting of halogen atoms, a cyano group, a nitro group, an epoxy group, cycloalkyl or cycloalkenyl groups having 5 to 7 carbon atoms as ring members, a phenyl group, a naphthyl group, groups $OR^{11}$, in which $R^{11}$ is a hydrogen atom, a hydrocarbon group having 1 to 15 carbon atoms which may be substituted or a hydrocarbon-carbonyl group having 2 to 16 carbon atoms which may be substituted.

10. The plant metabolism regulating agent of claim 1 wherein the hydrocarbon group represented by $R^2$, $R^3$, $R^4$, $R^5$, $R^7$, $R^8$, $R^9$ or $R^{10}$ or the hydrocarbon moiety represented by $R^7$ is substituted by a substituent selected from the class consisting of halogen atoms, a cyano group, a nitro group, an epoxy group, groups $OR^{11}$, and $R^{11}$, is as defined.

11. The plant metabolism regulating agent of claim 1 wherein the substituent of the hydrocarbon group represented by $R^2$, $R^3$, $R^4$, $R^5$, $R^7$, $R^8$, $R^9$ or $R^{10}$ or the hydrocarbon moiety represented by $R^7$ may further by a cycloalkyl or cycloalkenyl group having 5 to 7 carbon atoms as ring members, a phenyl group or a naphthyl group when the hydrocarbon group is an alkyl, alkenyl or alkynyl group; may further by an alkyl group having 1 to 7 carbon atoms, an alkenyl group having 2 to 7 carbon atoms, a phenyl group or a naphthyl group when the hydrocarbon group is a cycloalkyl or cycloalkenyl group; and may further be an alkyl group having 1 to 7 carbon atoms, an alkenyl group having 2 to 7 carbon atoms or a cycloalkyl or cycloalkenyl group having 5 to 7 carbon atoms as ring members when the hydrocarbon group is a phenyl group.

12. The plant metabolism regulating agent of claim 1 which is a herbicide.

13. The plant metabolism regulating agent of claim 1 which is a plant growth regulating agent.

14. The plant metabolism regulating agent of claim 1 which is a dwarfing agent.

15. A plant metabolism regulating agent comprising as an active ingredient an alpha,beta-unsaturated carboxylic acid or its derivative represented by the following formula (I)-a

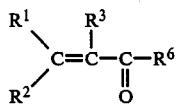

(I)-a wherein $R^1$ represents a hydrogen atom or a linear or branched aliphatic hydrocarbon group which has 1 to 5 unsaturated bonds selected from carbon-carbon double and triple bonds and in which the main chain has 2 to 15 carbon atoms;

wherein said aliphatic hydrocarbon group may be substituted by at least one substituent selected from the group consisting of a halogen atom, a cyano group, a nitro group, an epoxy group, a tetrahydropyranyloxy group, a cycloalkyl or cycloalkenyl group having 5 to 7 carbon atoms as ring members and the group $-OR^{11}$, wherein $R^{11}$ represents a hydrogen atom, a hydrocarbon group having 1 to 15 carbon atoms or a hydrocarbon-carbonyl group having 2 to 16 carbon atoms, wherein the hydrocarbon group or moiety for $R^{11}$ may be substituted by a substituent selected from the group consisting of alkyl groups having 1 to 7 carbon atoms, alkenyl groups having 2 to 7 carbon atoms, cycloalkyl or cycloalkenyl groups having 5 to 7 carbon atoms as ring members, a phenoxy group, an unsubstituted naphthoxy group and a pyridyloxy group, wherein the phenoxy group and the pyridyloxy group as the substituent of said hydrocarbon group or moiety may be substituted by a halogen atom, a cyano group, a nitro group, an unsubstituted or halogen-substituted alkyl group having 1 to 4 carbon atoms or the group $OR^{11}$;

R² represents a group selected from the group consisting of a hydrogen atom, halogen atom, a cyano group, a nitro group, an alkenyl or alkynyl group having 2 to 7 carbon atoms which may be substituted by said substituent for the hydrocarbon group or moiety for R¹¹, a cycloalkyl or cycloalkenyl group which has 3 to 7 carbon atoms as ring members and may be substituted by said substituent for the hydrocarbon group or moiety for R¹¹, or a phenyl group which may be substituted by said substituent for the hydrocarbon group or moiety for R¹¹, and groups OR⁷, in which R⁷ represents a hydrogen atom, a hydrocarbon group having 1 to 15 carbon atoms, a hydrocarbon-carbonyl group having 2 to 16 carbon atoms, a hydrocarbon-sulfonyl group having 1 to 15 carbon atoms or the group HSO₂—, wherein the hydrocarbon group or moiety for R⁷ may be substituted by said substituent for the hydrocarbon group or moiety for R¹¹;

R³ represents a group selected from said groups represented by R²; and

R⁶ represents a group selected from the group consisting of groups OR¹⁰ and groups NR⁸R⁹, in which R¹⁰ represents a hydrogen atom, one equivalent of a cation, or a hydrocarbon group having 1 to 15 carbon atoms which may be interrupted by an oxygen atom and R⁸ and R⁹ are identical or different, and each represents a hydrogen atom, a hydrocarbon group having 1 to 10 carbon atoms, a hydrocarbon-carbonyl group having 2 to 10 carbon atoms or a hydrocarbon-sulfonyl group having 1 to 10 carbon atoms, or R⁸ and R⁹ together may form a saturated, 5 to 6-membered ring containing, as a single heteroatom, the nitrogen atom to which they are bonded, wherein said one equivalent of a cation is selected from the group consisting of an alkali metal cation, one half of an alkaline earth metal cation and a primary, secondary, tertiary or quaternary ammonium cation of NH₄⁺ (in which R's are identical or different and each represents a hydrogen atom, an alkyl group having 1 to 6 carbon atoms, a phenyl group or a benzyl group), and said hydrocarbon group for R¹⁰, R⁸ and R⁹ may be substituted by said substituent for the hydrocarbon group or moiety for R¹¹; and R¹ cannot be a hydrogen atom or a methyl group and when R¹ has as the unsaturated bond a double bond conjugated with the double bond between the carbon atoms to which R¹ and R³ are bonded, the number of carbon atoms of the main change of R¹ cannot be more than 4, however, at least one of R¹, R² and R³ is a hydrocarbon group or moiety substituted by a phenoxy group or an unsubstituted naphthoxy group or a group having such a hydrocarbon group or moiety.

16. The plant metabolism regulating agent of claim 15 wherein R¹ is formula (I)-a is a linear or branched aliphatic hydrocarbon group having 2 to 15 carbon atoms which is substituted by a hydrocarbon-carbonyloxy group having 2 to 16 carbon atoms.

17. A plant metabolism regulating agent comprising as an active ingredient a beta,gamma-unsaturated carboxylic acid or its derivative represented by the following formula (I)-b

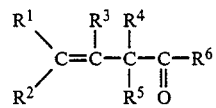

R¹ represents a hydrogen atom or a linear or branched aliphatic hydrocarbon group which has 1 to 5 unsaturated bonds selected from carbon-carbon double and triple bonds and in which the main chain has 2 to 15 carbon atoms;

wherein said aliphatic hydrocarbon group may be substituted by at least one substituent selected from the group consisting of a halogen atom, a cyano group, a nitro group, an epoxy group, a tetrahydropyranyloxy group, a cycloalkyl or cycloalkenyl group having 5 to 7 carbon atoms as ring members and the group —OR¹¹, wherein R¹¹ represents a hydrogen atom, a hydrocarbon group having 1 to 15 carbon atoms or a hydrocarbon-carbonyl group having 2 to 16 carbon atoms, wherein the hydrocarbon group or moiety for R¹¹ may be substituted by a substituent selected from the group consisting of alkyl groups having 1 to 7 carbon atoms, alkenyl groups having 2 to 7 carbon atoms, cycloalkyl or cycloalkenyl groups having 5 to 7 carbon atoms as ring members, a phenoxy group, an unsubstituted naphthoxy group and a pyridyloxy group, wherein the phenoxy group and the pyridyloxy group as the substituent of said hydrocarbon group or moiety may be substituted by a halogen atom, a cyano group, a nitro group, an unsubstituted or halogen-substituted alkyl group having 1 to 4 carbon atoms or the group OR¹¹;

R² represents a group selected from the group consisting of a hydrogen atom, halogen atom, a cyano group, a nitro group, an alkenyl or alkynyl group having 2 to 7 carbon atoms which may be substituted by said substituent for the hydrocarbon group or moiety for R¹¹, a cycloalkyl or cycloalkenyl group which has 3 to 7 carbon atoms as ring members and may be substituted by said substituent for the hydrocarbon group or moiety for R¹¹, or a phenyl group which may be substituted by said substituent for the hydrocarbon group or moiety for R¹¹, and groups OR⁷, in which R⁷ represents a hydrogen atom, a hydrocarbon group having 1 to 15 carbon atoms, a hydrocarbon-carbonyl group having 2 to 16 carbon atoms, a hydrocarbon-sulfonyl group having 1 to 15 carbon atoms or the group HSO₂—, wherein the hydrocarbon group or moiety for R⁷ may be substituted by said substituent for the hydrocarbon group or moiety for R¹¹;

R³ represents a group selected from said groups represented by R²;

R⁴ and R⁵ are identical or different and each represents a group selected from said groups represented by R²;

R⁶ represents a group selected from the group consisting of groups OR¹⁰ and groups NR⁸R⁹, in which R¹⁰ represents a hydrogen atom, one equivalent of a cation, or a hydrocarbon group having 1 to 15 carbon atoms which may be interrupted by an oxygen atom and R⁸ and R⁹ are identical or different, and each represents a hydrogen atom, a hydrocarbon group having 1 to 10 carbon atoms, a hydrocarbon-carbonyl group having 2 to 10 carbon atoms or a hydrocarbon-sulfonyl group having 1 to 10 carbon atoms, or $R^8$ and $R^9$ together may form a saturated, 5 to 6-membered ring containing, as a single heteroatom, the nitrogen atom to which they are bonded, wherein said one equivalent of a cation is selected from the group consisting of an alkali metal cation, one half of an alkaline earth metal cation and a primary, secondary, tertiary or quaternary ammonium cation of $NH_4^+$ (in which R's are identical or different and each represents a hydrogen atom, an alkyl group having 1 to 6 carbon atoms, a phenyl group or a benzyl group), and said hydrocarbon group for $R^{10}$, $R^8$ and $R^9$ may be substituted by said substituent for the hydrocarbon group or moiety for $R^{11}$; and when $R^1$, $R^2$ and $R^4$ are hydrogen atoms at the same time, $R^5$ cannot be a hydrogen atom or an unsubstituted hydrocarbon group having 1 to 15 carbon atoms, and when $R^1$ is a hydrogen atom and $R^2$ is an alkyl group having 1 to 2 carbon atoms, $R^4$ cannot be a hydrogen atom or an alkyl group having 1 to 2 carbon atoms, however, at least one of $R^1$, $R^2$, $R^3$, $R^4$ and $R^5$ is a hydrocarbon group or moiety substituted by a phenoxy group or an unsubstituted naphthoxy group or a group having such a hydrocarbon group or moiety.

18. A method of controlling the metabolism of a plant, which comprising applying an alpha,beta- or beta,gamma-unsaturated carboxylic acid or its derivative represented by formula (I) below

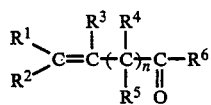

(I)

wherein $R^1$ represents a hydrogen atom or a linear or branched aliphatic hydrocarbon group which has 1 to 5 unsaturated bonds selected from carbon-carbon double and triple bonds and in which the main chain has 2 to 15 carbon atoms;

wherein said aliphatic hydrocarbon group may be substituted by at least one substituent selected from the group consisting of a halogen atom, a cyano group, a nitro group, an epoxy group, a tetrahydropyranyloxy group, a cycloalkyl or cycloalkenyl group having 5 to 7 carbon atoms as ring members and the group —$OR^{11}$, wherein $R^{11}$ represents a hydrogen atom, a hydrocarbon group having 1 to 15 carbon atoms or a hydrocarbon-carbonyl group having 2 to 16 carbon atoms, wherein the hydrocarbon group or moiety for $R^{11}$ may be substituted by a substituent selected from the group consisting of alkyl groups having 1 to 7 carbon atoms, alkenyl groups having 2 to 7 carbon atoms, cycloalkyl or cycloalkenyl groups having 5 to 7 carbon atoms as ring members, a phenoxy group, an unsubstituted naphthoxy group and a pyridyloxy group, wherein the phenoxy group and the pyridyloxy group as the substituent of said hydrocarbon group or moiety may be substituted by a halogen atom, a cyano group, a nitro group, an unsubstituted or halogen-substituted alkyl group having 1 to 4 carbon atoms or the group $OR^{11}$;

$R^2$ represents a group selected from the group consisting of a hydrogen atom, halogen atom, a cyano group, a nitro group, an alkenyl or alkynyl group having 2 to 7 carbon atoms which may be substituted by said substituent for the hydrocarbon group or moiety for $R^{11}$, a cycloalkyl or cycloalkenyl group which has 3 to 7 carbon atoms as ring members and may be substituted by said substituent for the hydrocarbon group or moiety for $R^{11}$, or a phenyl group which may be substituted by said substituent for the hydrocarbon group or moiety for $R^{11}$, and groups $OR^7$, in which $R^7$ represents a hydrogen atom, a hydrocarbon group having 1 to 15 carbon atoms, a hydrocarbon-carbonyl group having 2 to 16 carbon atoms, a hydrocarbon-sulfonyl group having 1 to 15 carbon atoms or the group $HSO_2$—, wherein the hydrocarbon group or moiety for $R^7$ may be substituted by said substituent for the hydrocarbon group or moiety for $R^{11}$;

$R^3$ represents a group selected from said groups represented by $R^2$;

$R^4$ and $R^5$ are identical or different and each represents a group selected from said groups represented by $R^2$;

$R^6$ represents a group selected from the group consisting of groups $OR^{10}$ and groups $NR^8R^9$, in which $R^{10}$ represents a hydrogen atom, one equivalent of a cation, or a hydrocarbon group having 1 to 15 carbon atoms which may be interrupted by an oxygen atom and $R^8$ and $R^9$ are identical or different, and each represents a hydrogen atom, a hydrocarbon group having 1 to 10 carbon atoms, a hydrocarbon-carbonyl group having 2 to 10 carbon atoms or a hydrocarbon-sulfonyl group having 1 to 10 carbon atoms, or $R^8$ and $R^9$ together may form a saturated, 5 to 6-membered ring containing, as a single heteroatom, the nitrogen atom to which they are bonded, wherein said one equivalent of a cation is selected from the group consisting of an alkali metal cation, one half of an alkaline earth metal cation and a primary, secondary, tertiary or quaternary ammonium cation of $NH_4^+$ (in which R's are identical or different and each represents a hydrogen atom, an alkyl group having 1 to 6 carbon atoms, a phenyl group or a benzyl group), and said hydrocarbon group for $R^{10}$, $R^8$ and $R^9$ may be substituted by said substituent for the hydrocarbon group or moiety for $R^{11}$; and n is 0 or 1 provided that (1) in the case of n=0, $R^1$ cannot be a hydrogen atom or a methyl group and when $R^1$ has as the unsaturated bond a double bond conjugated with the double bond between the carbon atoms to which $R^1$ and $R^3$ are bonded, the number of carbon atoms of the main chain of $R^1$ cannot be more than 4, and (2) in the case of n=1, when $R^1$, $R^2$ and $R^4$ are hydrogen atoms at the same time, $R^5$ cannot be a hydrogen atom or an unsubstituted hydrocarbon group having 1 to 15 carbon atoms, and when $R^1$ is a hydrogen atom and $R^2$ is an alkyl group having 1 to 2 carbon atoms, $R^4$ cannot be a hydrogen atom or an alkyl group having 1 to 2 carbon atoms, however, at least one of $R^1$, $R^2$, $R^3$, $R^4$ and $R^5$ is a hydrocarbon group or moiety substituted by a phenoxy group or an unsubstituted naphthoxy group or a group having such a hydrocarbon group or moiety, or a composition containing it as an active ingredient to a plant whose metabolism is to be regulated, seeds of such a plant, or a locus where such a plant is growing or its growth is anticipated in an amount sufficient to regulate the metabolism of the plant.

19. A method for facilitating the growth of a beneficial plant by inhibiting the growth of undesirable plants or eradicating them, which comprises applying an alpha,beta- or beta,gamma-unsaturated carboxylic acid or its derivative represented by formula (I) below

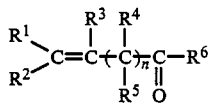

wherein $R^1$ represents a hydrogen atom or a linear or branched aliphatic hydrocarbon group which has 1 to 5 unsaturated bonds selected from carbon-carbon double and triple bonds and in which the main chain has 2 to 15 carbon atoms;

wherein said aliphatic hydrocarbon group may be substituted by at least one substituent selected from the group consisting of a halogen atom, a cyano group, a nitro group, an epoxy group, a tetrahydropyranyloxy group, a cycloalkyl or cycloalkenyl group having 5 to 7 carbon atoms as ring members and the group $-OR^{11}$, wherein $R^{11}$ represents a hydrogen atom, a hydrocarbon group having 1 to 15 carbon atoms or a hydrocarbon-carbonyl group having 2 to 16 carbon atoms, wherein the hydrocarbon group or moiety for $R^{11}$ may be substituted by a substituent selected from the group consisting of alkyl groups having 1 to 7 carbon atoms, alkenyl groups having 2 to 7 carbon atoms, cycloalkyl or cycloalkenyl groups having 5 to 7 carbon atoms as ring members, a phenoxy group, an unsubstituted naphthoxy group and a pyridyloxy group, wherein the phenoxy group and the pyridyloxy group as the the substituent of said hydrocarbon group or moiety may be substituted by a halogen atom, a cyano group, a nitro group, an unsubstituted or halogen-substituted alkyl group having 1 to 4 carbon atoms or the group $OR^{11}$;

$R^2$ represents a group selected from the group consisting of a hydrogen atom, halogen atom, a cyano group, a nitro group, an alkenyl or alkynyl group having 2 to 7 carbon atoms which may be substituted by said substituent for the hydrocarbon group or moiety for $R^{11}$, a cycloalkyl or cycloalkenyl group which has 3 to 7 carbon atoms as ring members and may be substituted by said substituent for the hydrocarbon group or moiety for $R^{11}$, or a phenyl group which may be substituted by said substituent for the hydrocarbon group or moiety for $R^{11}$, and groups $OR^7$, in which $R^7$ represents a hydrogen atom, a hydrocarbon group having 1 to 15 carbon atoms, a hydrocarbon-carbonyl group having 2 to 16 carbon atoms, a hydrocarbon-sulfonyl group having 1 to 15 carbon atoms or the group $HSO_2-$, wherein the hydrocarbon group or moiety for $R^7$ may be substituted by said substituent for the hydrocarbon group or moiety for $R^{11}$;

$R^3$ represents a group selected from said groups represented by $R^2$;

$R^4$ and $R^5$ are identical or different and each represents a group selected from said groups represented by $R^2$;

$R^6$ represents a group selected from the group consisting of groups $OR^{10}$ and groups $NR^8R^9$, in which $R^{10}$ represents a hydrogen atom, one equivalent of a cation, or a hydrocarbon group having 1 to 15 carbon atoms which may be interrupted by an oxygen atom and $R^8$ and $R^9$ are identical or different, and each represents a hydrogen atom, a hydrocarbon group having 1 to 10 carbon atoms, a hydrocarbon-carbonyl group having 2 to 10 carbon atoms or a hydrocarbon-sulfonyl group having 1 to 10 carbon atoms, or $R^8$ and $R^9$ together may form a saturated, 5 to 6-membered ring containing, as a single heteroatom, the nitrogen atom to which they are bonded, wherein said one equivalent of a cation is selected from the group consisting of an alkali metal cation, one half of an alkaline earth metal cation and a primary, secondary, tertiary or quaternary ammonium cation of $NR_4^+$ (in which R's are identical or different and each represents a hydrogen atom, an alkyl group having 1 to 6 carbon atoms, a phenyl group or a benzyl group), and said hydrocarbon group for $R^{10}$, $R^8$ and $R^9$ may be substituted by said substituent for the hydrocarbon group or moiety for $R^{11}$; and n is 0 or 1 provided that (1) in the case of n=0, $R^1$ cannot be a hydrogen atom or a methyl group and when $R^1$ has as the unsaturated bond a double bond conjugated with the double bond between the carbon atoms to which $R^1$ and $R^3$ are bonded, the number of carbon atoms of the main chain of $R^1$ cannot be more than 4, and (2) in the case of n=1, when $R^1$, $R^2$ and $R^4$ are hydrogen atoms at the same time, $R^5$ cannot be a hydrogen atom or an unsubstituted hydrocarbon group having 1 to 15 carbon atoms, and when $R^1$ is a hydrogen atom and $R^2$ is an alkyl group having 1 to 2 carbon atoms, $R^4$ cannot be a hydrogen atom or an alkyl group having 1 to 2 carbon atoms, however, at least one of $R^1$, $R^2$, $R^3$, $R^4$ and $R^5$ is a hydrocarbon group or moiety substituted by a phenoxy group or an unsubstituted naphthoxy group or a group having such a hydrocarbon group or moiety, or a composition containing it as an active ingredient either directly to the beneficial plant or its seeds or to the soil in a locus where the beneficial plant or its seeds and the undesirable plants of their seeds exist together or are likely to exist together in an amount sufficient to inhibit the growth of the undesirable plants or eradicate them.

20. The method of claim 18 wherein the beneficial plant is a plant which produces cereals, a plant at least a part of which is useful as a feed, or lawn.

21. The method of claim 20 wherein the beneficial plant which produces cereals is rice or corn.

22. A method of regulating the growth of a plant, which comprises applying an alpha,beta- or beta,gamma-unsaturated carboxylic acid or its derivative represented by formula (I) below

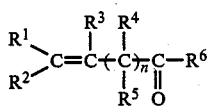

wherein $R^1$ represents a hydrogen atom or a linear or branched aliphatic hydrocarbon group which has 1 to 5 unsaturated bonds selected from carbon-carbon double and triple bonds and in which the main chain has 2 to 15 carbon atoms;

wherein said aliphatic hydrocarbon group may be substituted by at least one substituent selected from the group consisting of a halogen atom, a cyano group, a nitro group, an epoxy group, a tetrahydropyranyloxy group, a cycloalkyl or cycloalkenyl group having 5 to 7 carbon atoms as ring members and the group $-OR^{11}$, wherein $R^{11}$ represents a hydrogen atom, a hydrocarbon group having 1 to 15 carbon atoms or a hydrocarbon-carbonyl group having 2 to 16 carbon atoms, wherein the hydrocarbon group or moiety for $R^{11}$ may be substituted by a substituent selected from the group consisting of alkyl groups having 1 to 7 carbon atoms, alkenyl groups having 2 to 7 carbon atoms, cycloalkyl or cycloalkenyl groups having 5 to 7 carbon atoms as ring members, a phenoxy group, an unsubstituted naphthoxy group and a pyridyloxy group, wherein the phenoxy group and the pyridyloxy group as the substituent of said hydrocarbon group or moiety may be substituted by a halogen atom, a cyano group, a nitro group, an unsubstituted or halogen-substituted alkyl group having 1 to 4 carbon atoms or the group $OR^{11}$, $R^2$ represents a group selected from the group consisting of a hydrogen atom, halogen atom, a cyano group, a nitro group, an alkenyl or alkenyl group having 2 to 7 carbon atoms which may be substituted by said substituent for the hydrocarbon group or moiety for $R^{11}$, a cycloalkyl or cycloalkenyl group which has 3 to 7 carbon atoms as ring members and may be substituted by said substituent for the hydrocarbon group or moiety for $R^{11}$, or a phenyl group which may be substituted by said substituent for the hydrocarbon group or moiety for $R^{11}$, and groups $OR^7$, in which $R^7$ represents a hydrogen atom, a hydrocarbon group having 1 to 15 carbon atoms, a hydrocarbon-carbonyl group having 2 to 16 carbon atoms, a hydrocarbon-sulfonyl group having 1 to 15 carbon atoms or the group $HSO_2-$, wherein the hydrocarbon group or moiety for $R^7$ may be substituted by said substituent for the hydrocarbon group or moiety for $R^{11}$;

$R^3$ represents a group selected from said groups represented by $R^2$;

$R^4$ and $R^5$ are identical or different and each represents a group selected from said groups represented by $R^2$;

$R^6$ represents a group selected from the group consisting of groups $OR^{10}$ and groups $NR^8R^9$, in which $R^{10}$ represents a hydrogen atom, one equivalent of a cation, or a hydrocarbon group having 1 to 15 carbon atoms which may be interrupted by an oxygen atom and $R^8$ and $R^9$ are identical or different, and each represents a hydrogen atom, a hydrocarbon group having 1 to 10 carbon atoms, a hydrocarbon-carbonyl group having 2 to 10 carbon atoms or a hydrocarbon-sulfonyl group having 1 to 10 carbon atoms, or $R^8$ and $R^9$ together may form a saturated, 5 to 6-membered ring containing, as a single heteroatom, the nitrogen atom to which they are bonded, wherein said one equivalent of a cation is selected from the group consisting of an alkali metal cation, one half of an alkaline earth metal cation and a primary, secondary, tertiary or quaternary ammonium cation of $NH_4^+$ (in which R's are identical or different and each represents a hydrogen atom, an alkyl group having 1 to 6 carbon atoms, a phenyl group or a benzyl group), and said hydrocarbon group for $R^{10}$, $R^8$ and $R^9$ may be substituted by said substituent for the hydrocarbon group or moiety for $R^{11}$; and n is 0 or 1 provided that (1) in the case of n=0, $R^1$ cannot be a hydrogen atom or a methyl group and when $R^1$ has as the unsaturated bond a double bond conjugated with the double bond between the carbon atoms to which $R^1$ and $R^3$ are bonded, the number of carbon atoms of the main chain of $R^1$ cannot be more than 4, and (2) in the case of n=1, when $R^1$, $R^2$ and $R^4$ are hydrogen atoms at the same time, $R^5$ cannot be a hydrogen atom or an unsubstituted hydrocarbon group having 1 to 15 carbon atoms, and when $R^1$ is a hydrogen atom and $R^2$ is an alkyl group having 1 to 2 carbon atoms, $R^4$ cannot be a hydrogen atom or an alkyl group having 1 to 2 carbon atoms, however, at least one of $R^1$, $R^2$, $R^3$, $R^4$ and $R^5$ is a hydrocarbon group or moiety substituted by a phenoxy group or an unsubstituted naphthoxy group or a group having such a hydrocarbon group or moiety, or a composition containing it as an active ingredient to a plant whose growth is to be regulated, its seeds or a locus where such a plant is growing or its growth is anticipated in an amount sufficient to regulate the growth of the plant.

23. A method of dwarfing a plant, which comprises applying an alpha,beta- or beta,gamma-unsaturated carboxylic acid or its derivative represented by formula (I) below

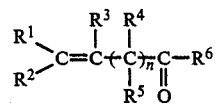

wherein $R^1$ represents a hydrogen atom or a linear or branched aliphatic hydrocarbon group which has 1 to 5 unsaturated bonds selected from carbon-carbon double and triple bonds and in which the main chain has 2 to 15 carbon atoms;

wherein said aliphatic hydrocarbon group may be substituted by at least one substituent selected from the group consisting of a halogen atom, a cyano group, a nitro group, and epoxy group, a tetrahydropyranyloxy group, a cycloalkyl or cycloalkenyl group having 5 to 7 carbon atoms as ring members and the group $-OR^{11}$, wherein $R^{11}$ represents a hydrogen atom, a hydrocarbon group having 1 to 15 carbon atoms or a hydrocarbon-carbonyl group having 2 to 16 carbon atoms, wherein the hydrocarbon group or moiety for $R^{11}$ may be substituted by a substituent selected from the group consisting of alkyl groups having 1 to 7 carbon atoms, alkenyl groups having 2 to 7 carbon atoms, cycloalkyl or cycloalkenyl groups having 5 to 7 carbon atoms as ring members, a phenoxy group, an unsubstituted naphthoxy group and a pyridyloxy group, wherein the phenoxy group and the pyridyloxy group as the substituent of said hydrocarbon group or moiety may be substituted by a halogen atom, a cyano group, a nitro group, an unsubstituted or halogen-substituted alkyl group having 1 to 4 carbon atoms or the group $OR^{11}$;

$R^2$ represents a group selected from the group consisting of a hydrogen atom, halogen atom, a cyano group, a nitro group, an alkenyl or alkynyl group having 2 to 7 carbon atoms which may be substituted by said substituent for the hydrocarbon group or moiety for $R^{11}$, a cycloalkyl or cycloalkenyl group which has 3 to 7 carbon atoms as ring members and may be substituted by said substituent for the hydrocarbon group or moiety for $R^{11}$, or a phenyl group which may be substituted by said substituent for the hydrocarbon group or moiety for $R^{11}$, and groups $OR^7$, in which $R^7$ represents a hydrogen atom, a hydrocarbon group having 1 to 15 carbon atoms, a hydrocarbon-carbonyl group having 2 to 16 carbon atoms, a hydrocarbon-sulfonyl group having 1 to 15 carbon atoms or the group $HSO_2-$, wherein the hydrocarbon group or moiety for $R^7$ may be substituted by said substituent for the hydrocarbon group or moiety for $R^{11}$; p1 $R^3$ represents a group selected from said groups represented by $R^2$;

$R^4$ and $R^5$ are identical or different and each represents a group selected from said groups represented by $R^2$;

$R^6$ represents a group selected from the group consisting of groups $OR^{10}$ and groups $NR^8R^9$, in which $R^{10}$ represents a hydrogen atom, one equivalent of a cation, or a hydrocarbon group having 1 to 15 carbon atoms which may be interrupted by an oxygen atom and $R^8$ and $R^9$ are identical or different, and each represents a hydrogen atom, a hydrocarbon group having 1 to 10 carbon atoms, a hydrocarbon-carbonyl group having 2 to 10 carbon atoms or a hydrocarbon-sulfonyl group having 1 to 10 carbon atoms, or $R^8$ and $R^9$ together may form a saturated, 5 to 6-membered ring containing, as a single heteroatom, the nitrogen atom to which they are bonded, wherein said one equivalent of a cation is selected from the group consisting of an alkali metal cation, one half of an alkaline earth metal cation and a primary, secondary, tertiary or quaternary ammonium cation of $NH_4^+$ (in which R's are identical or different and each represents a hydrogen atom, an alkyl group having 1 to 6 carbon atoms, a phenyl group or a benzyl group), and said hydrocarbon group for $R^{10}$, $R^8$ and $R^9$ may be substituted by said substituent for the hydrocarbon group or moiety for $R^{11}$; and n is 0 or 1 provided that (1) in the case of n=0, $R^1$ cannot be a hydrogen atom or a methyl group and when $R^1$ has as the unsaturated bond a double bond conjugated with the double bond between the carbon atoms to which $R^1$ and $R^3$ are bonded, the number of carbon atoms of the main chain of $R^1$ cannot be more than 4, and (2) in the case of n=1, when $R^1$, $R^2$ and $R^4$ are hydrogen atoms at the same time, $R^5$ cannot be a hydrogen atom or an unsubstituted hydrocarbon group having 1 to 15 carbon atoms, and when $R^1$ is a hydrogen atom and $R^2$ is an alkyl group having 1 to 2 carbon atoms, $R^4$ cannot be a hydrogen atom or an alkyl group having 1 to 2 carbon atoms, however, at least one of $R^1$, $R^2$, $R^3$, $R^4$ and $R^5$ is a hydrocarbon group or moiety substituted by a phenoxy group or an unsubstituted naphthoxy group or a group having such a hydrocarbon group or moiety, or a composition containing it as an active ingredient to a plant to be dwarfed, its seeds or a locus where such plant is growing or its growth is anticipated in an amount sufficient to dwarf the plant.

24. The plant metabolism regulating agent of claim 16 wherein the hydrocarbon-carbonyloxy group having 2 to 16 carbon atoms is in turn substituted by a substituted aromatic oxy group, said substituted aromatic oxy group being a phenoxy, naphthyloxy, phenoxyphenoxy or pyridyloxyphenoxy group substituted by a substituent selected from the group consisting of halogen atoms, a cyano group, a nitro group, unsubstituted or halogen-substituted alkyl groups having 1 to 4 carbon atoms, groups $OR^{11}$, groups $SR^{11}$ and groups $NR^8R^9$.

25. The plant metabolism regulating agent of claim 17 wherein in formula (I)-b, $R^5$ is the group $OR^7$ or

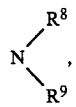

$R^7$ is a hydrocarbon-carbonyloxy group having 2 to 16 carbon atoms, each of $R^8$ and $R^9$ is a hydrocarbon-carbonyl group having 1 to 10 carbon atoms and each of said hydrocarbon-carbonyloxy groups having 2 to 16 carbon atoms and having 1 to 10 carbon atoms may be in turn substituted by a substituted aromatic oxy group, said aromatic oxy group being a phenoxy, naphthyloxy, phenoxyphenoxy or pyridyloxyphenoxy group substituted by a substituent selected from the group consisting of halogen atoms, a cyano group, a nitro group, unsubstituted or halogen-substituted alkyl groups having 1 to 4 carbon atoms, groups $OR^{12}$, groups $SR^{12}$ and groups $NR^8R^9$.

* * * * *